US008808624B2

(12) United States Patent
Matsumoto et al.

(10) Patent No.: US 8,808,624 B2
(45) Date of Patent: Aug. 19, 2014

(54) BLOOD ANALYZER, BLOOD ANALYSIS METHOD AND HEMOLYTIC AGENT

(75) Inventors: Hideaki Matsumoto, Takasago (JP); Kinya Uchihashi, Kakogawa (JP); Yuji Itose, Kako-gun (JP); Aya Konishi, Nishinomiya (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/942,561

(22) Filed: Nov. 9, 2010

(65) Prior Publication Data

US 2011/0053210 A1    Mar. 3, 2011

Related U.S. Application Data

(63) Continuation of application No. PCT/JP2009/058316, filed on Apr. 28, 2009.

(30) Foreign Application Priority Data

May 9, 2008   (JP) ................... 2008-123347
May 9, 2008   (JP) ................... 2008-123388

(51) Int. Cl.
*G01N 33/00*   (2006.01)

(52) U.S. Cl.
USPC .................. 422/73; 422/62; 422/63; 422/64; 422/65; 422/66; 422/67; 422/68.1; 422/81; 422/82.05; 422/82.08; 422/82.09; 436/8; 436/10; 436/43; 436/52; 436/164; 436/172

(58) Field of Classification Search
CPC ............... G01N 15/1456; G01N 2015/0073; G01N 2015/0088; G01N 2015/1477; G01N 33/5094; G01N 33/52; G01N 33/54313; G01N 33/80; G01N 15/12; G01N 15/1459; G01N 1/38; G01N 2015/0084; G01N 2015/0092; G01N 2015/1486; G01N 33/86; G01N 35/00584; G01N 2015/0065; G01N 21/6428; G01N 33/53; G01N 33/54366; G01N 33/56905; G01N 33/582; G01N 15/147; G01N 2015/0076; G01N 2015/008; G01N 2021/4726; G01N 2021/6439; G01N 2021/6482; G01N 2021/6493; G01N 21/05; G01N 21/47; G01N 21/51; G01N 21/6486; G01N 2333/44; G01N 33/49; G01N 33/5047
USPC .......... 422/62–67, 68.1, 73, 81, 82.05, 82.08, 422/82.09; 436/8, 10, 43, 52, 164, 172; 700/266; 702/19, 21, 22, 23, 25, 26
See application file for complete search history.

(56) References Cited

U.S. PATENT DOCUMENTS 5,250,437 A   10/1993   Toda et al.
5,496,734 A    3/1996   Sakata
(Continued)

FOREIGN PATENT DOCUMENTS

CN   1980664 A   6/2007
JP   2836865 B2   6/1991
(Continued)

OTHER PUBLICATIONS

Kohsuke Sasaki, et al., "Fluorescent Cytochemistry for Flow Cytometry", The Cell, 1985, pp. 357-360, vol. 17, No. 8.
(Continued)

*Primary Examiner* — Dean Kwak
(74) *Attorney, Agent, or Firm* — Sughrue Mion, PLLC

(57) ABSTRACT

This blood analyzer includes a sample preparation portion preparing a measurement sample free from a labeling substance from a blood sample and a hemolytic agent free from a labeling substance, a light information generation portion generating fluorescent information and at least two types of scattered light information from the measurement sample and a control portion performing a first classification of white blood cells in the measurement sample into at least four groups of monocytes, neutrophils, eosinophils and others on the basis of the fluorescent information and the two types of scattered light information.

14 Claims, 18 Drawing Sheets

(56) References Cited

U.S. PATENT DOCUMENTS

| | | | |
|---|---|---|---|
| 5,538,893 | A | 7/1996 | Sakata et al. |
| 5,618,733 | A | 4/1997 | Sakata et al. |
| 5,763,280 | A | 6/1998 | Li et al. |
| 5,817,518 | A | 10/1998 | Li et al. |
| 5,882,934 | A | 3/1999 | Li et al. |
| 6,772,650 | B2 | 8/2004 | Ohyama et al. |
| 6,938,502 | B2 | 9/2005 | Tanoshima et al. |
| 7,633,604 | B2 | 12/2009 | Ikeuchi et al. |
| 2005/0202400 | A1* | 9/2005 | Tsuji et al. .................. 435/4 |
| 2005/0219527 | A1 | 10/2005 | Ikeuchi et al. |
| 2006/0029520 | A1 | 2/2006 | Tanoshima et al. |
| 2006/0210438 | A1 | 9/2006 | Nagai et al. |
| 2006/0250604 | A1* | 11/2006 | Hamada et al. ............. 356/39 |
| 2007/0020721 | A1* | 1/2007 | Yoshida et al. ............. 435/34 |

FOREIGN PATENT DOCUMENTS

| | | | |
|---|---|---|---|
| JP | 3345135 | B2 | 7/1994 |
| JP | 3320869 | B2 | 7/1995 |
| JP | 07-294518 | A | 11/1995 |
| JP | 3717939 | B2 | 2/2000 |
| JP | 2001-509273 | A | 7/2001 |
| JP | 2003-083960 | A | 3/2003 |
| JP | 2005-077398 | A | 3/2005 |
| JP | 2005-257450 | A | 9/2005 |
| JP | 2006-091024 | A | 4/2006 |
| JP | 2006-292738 | A | 10/2006 |
| WO | 2005/115382 | A1 | 12/2005 |

OTHER PUBLICATIONS

Jennifer P. Day, et al., "Differentiation of *Phytophthora infestans* Sporangia from Other Airborne Biological Particles by Flow Cytometry", Applied and Environmental Microbiology, Jan. 2002, pp. 37-45, vol. 68, No. 1.

Michael Y. Viksman, et al., "Application of a Flow Cytometric Method Using Autofluorescence and a Tandem Fluorescent Dye to Analyze Human Alveolar Macrophage Surface Markers", Journal of Immunological Methods, 1994, pp. 17-24, vol. 172, No. 1.

Toshiyuki Ikemoto, et al., "Comparison Between a Specific Gravity Separation Method and a Whole Blood Lysis Method in Sample Preparation", Molecular Medicine, 2002, pp. 592-595, vol. 39, No. 5.

Tsuruda Kazuto, et al., "Gating (Setting of Cell Analysis Region)", Molecular Medicine, 2002, pp. 712-719. vol. 39, No. 6.

J. Linseen, et al., "Identification and Quantification of High Fluorescence-Stained Lymphocytes as Antibody Synthesizing/Secreting Cells Using the Automated Routine Hematology Analyzer XE-2100", Cytometry Part B (Clinical Cytometry), 2007, pp. 157-166, 72B.

* cited by examiner

FIG.10

COMPOSITION OF HEMOLYTIC AGENT

| LAURYL TRIMETHYL AMMONIUM CHLORIDE | 34.1 mM |
|---|---|
| STEARYL TRIMETHYL AMMONIUM CHLORIDE | 1.7 mM |
| EDTA-2K | 1.0 g/L |
| PHOSPHATE BUFFER SOLUTION | 20 mM(pH 5.0) |
| NaCl | PROPER QUANTITY (QUANTITY TO MAKE ELECTRIC CONDUCTIVITY BE ABOUT 13 mS/cm) |
| PURIFIED WATER | 1 L |

FIG.11

STAINING FLUID (FOR MALARIA DETECTION)

[CHEMICAL FORMULA OF FLUORESCENT DYE]

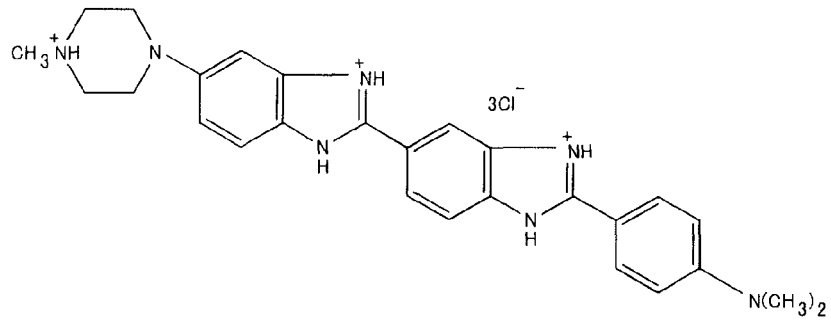

[NONIONIC SURFACTANT GROUP]

POLYOXYETHYLENE SORBITAN MONOISOSTEARATE,
POLYOXYETHYLENE SORBITAN MONOOLEATE,
POLYOXYETHYLENE HYDROGENATED CASTOR OIL,
POLYOXYETHYLENE PHYTOSTEROL,
POLYOXYETHYLENE PHYTOSTANOL,
POLYOXYETHYLENE LAURYL ETHER,
POLYOXYETHYLENE OLEYL ETHER,
POLYOXYETHYLENE POLYOXYPROPYLENE DECYL TETRADECYL ETHER,
POLYOXYETHYLENE POLYOXYPROPYLENE CETYL ETHER,
POLYOXYETHYLENE MONOLAURATE

WBC PARTICLE SIZE DISTRIBUTION

BLOOD ANALYZER, BLOOD ANALYSIS METHOD AND HEMOLYTIC AGENT

CROSS-REFERENCE TO RELATED APPLICATION

The priority application number JP2008-123347, Blood Analyzer, Blood Analysis Method and Hemolytic Agent, May 9, 2008, Hideaki Matsumoto, Kinya Uchihashi, Yuji Itose, Aya Konishi, and JP2008-123388, Blood Analyzer, Blood Analysis Method and Hemolytic Agent, May 9, 2008, Hideaki Matsumoto, Kinya Uchihashi, Yuji Itose, Aya Konishi upon which this patent application is based are hereby incorporated by reference. This application is a continuation of PCT/JP2009/058316, Blood Analyzer, Blood Analysis Method and Hemolytic Agent, Apr. 28, 2009, Hideaki Matsumoto, Kinya Uchihashi, Yuji Itose, Aya Konishi.

BACKGROUND OF THE INVENTION

1. Field of the Invention

The present invention relates to a blood analyzer, a blood analysis method and a hemolytic agent.

2. Description of the Background Art

A blood analyzer classifying white blood cells is known in general. Such a blood analyzer is disclosed in each of Japanese Patent Laying-Open No. 2003-83960 and Japanese Patent Laying-Open No. 2005-257450, for example.

A blood analyzer described in the aforementioned Japanese Patent Laying-Open No. 2003-83960 comprises an electrical resistance type detection unit detecting white blood cells in a measurement sample prepared from a blood sample and a reagent and is configured to classify the white blood cells in the measurement sample into three groups on the basis of a detection result by the electrical resistance type detection unit.

A blood analyzer described in the aforementioned Japanese Patent Laying-Open No. 2005-257450 comprises a sample preparation unit preparing a measurement sample from a blood sample and a reagent and an optical detection unit detecting forward scattered light, lateral scattered light and fluorescent light and is configured to classify white blood cells in the measurement sample into four groups on the basis of a detection result by the optical detection unit. This optical detection unit detects fluorescent light of fluorescently-labeled white blood cells.

However, there is such a problem that the blood analyzer according to the aforementioned Japanese Patent Laying-Open No. 2003-83960 cannot classify the white blood cells in the measurement sample into more than three groups.

In the blood analyzer according to the aforementioned Japanese Patent Laying-Open No. 2005-257450, the white blood cells in the measurement sample must be fluorescently-labeled while the white blood cells in the measurement sample can be classified into four groups, and hence there is such inconvenience that an expensive reagent containing a labeling substance must be employed. Thus, a blood analyzer capable of classifying white blood cells into more than three groups and requiring no reagent containing a labeling substance is desired.

A blood analyzer classifying white blood cells and acquiring a hemoglobin concentration is known in general. Such a blood analyzer is disclosed in Japanese Patent Laying-Open No. 2006-292738, for example.

A blood analyzer described in the aforementioned Japanese Patent Laying-Open No. 2006-292738 is configured to measure forward scattered light, lateral scattered light and fluorescent light employing a measurement sample containing a blood sample and a reagent for classifying white blood cells and classify white blood cells in the measurement sample into four groups. This blood analyzer is configured to detect transmitted light employing a measurement sample containing a blood sample and a dedicated reagent for measuring hemoglobin having a different composition from the reagent for classifying white blood cells and acquire a hemoglobin concentration in the measurement sample.

However, the blood analyzer according to the aforementioned Japanese Patent Laying-Open No. 2006-292738 classifies white blood cells employing the reagent for classifying white blood cells and acquires a hemoglobin concentration employing the dedicated reagent for measuring hemoglobin having a different composition from the reagent for classifying white blood cells, and hence two types of reagents having different compositions from each other must be developed separately to classify white blood cells and acquire a hemoglobin concentration. Consequently, there is such a problem that the prices of the reagents rise thereby straining a user.

SUMMARY OF THE INVENTION

A blood analyzer according to a first aspect of the present invention comprises a sample preparation portion preparing a measurement sample free from a labeling substance from a blood sample and a hemolytic agent free from a labeling substance; a light information generation portion generating fluorescent information and at least two types of scattered light information from the measurement sample prepared by the sample preparation portion, and a control portion performing a first classification of white blood cells in the measurement sample into at least four groups of monocytes, neutrophils, eosinophils and others on the basis of the fluorescent information and the two types of scattered light information.

In the aforementioned blood analyzer according to the first aspect, the light information generation portion is preferably configured to generate the fluorescent information on the basis of intrinsic fluorescence of the eosinophils in the measurement sample.

In the aforementioned blood analyzer according to the first aspect, the sample preparation portion preferably prepares a second measurement sample containing the blood sample and a predetermined hemolytic agent, and the blood analyzer preferably further comprises an electrical information generation portion generating electrical information of a sample from the second measurement sample, wherein the control portion is configured to perform a second classification of white blood cells in the second measurement sample into at least lymphocytes and others on the basis of the electrical information generated by the electrical information generation portion and classify the white blood cells in the measurement sample into at least five groups of lymphocytes, basophils, monocytes, neutrophils and eosinophils on the basis of classification results of the first classification and the second classification.

In the aforementioned blood analyzer according to the first aspect, the light information generation portion preferably includes: a light source; a fluorescence receiving portion receiving fluorescence occurred by emitting a beam of light from the light source to the measurement sample and generating the fluorescent information corresponding to an intensity of the received fluorescence; and a scattered light receiving portion receiving scattered light occurred by emitting a beam of light from the light source to the measurement sample and generating the scattered light information corresponding to an intensity of the received scattered light.

In this case, the scattered light receiving portion preferably comprises: a first receiving portion receiving forward scattered light occurred along a traveling direction of the beam of light emitted from the light source and generating forward scattered light information corresponding to an intensity of the received forward scattered light; and a second receiving portion receiving side scattered light occurred along a direction substantially perpendicular to the traveling direction of the beam of light emitted from the light source and generating side scattered light information corresponding to an intensity of the received side scattered light.

In the aforementioned structure in which the scattered light receiving portion has the first receiving portion and the second receiving portion, the control portion is preferably configured to classify the white blood cells in the measurement sample into at least the eosinophils and others on the basis of the forward scattered light information and the fluorescent information.

In the aforementioned structure in which the light information generation portion includes the light source, the beam of light which is emitted from the light source has a wavelength of at least 350 nm and not more than 500 nm.

In the aforementioned structure in which the light source emits light having a wavelength in a predetermined range, the light source preferably has a blue-violet semiconductor laser element.

A blood analysis method according to a second aspect of the present invention comprises preparing a measurement sample free from a labeling substance from a blood sample and a hemolytic agent free from a labeling substance, generating fluorescent information and at least two types of scattered light information from the prepared measurement sample, and classifying white blood cells in the measurement sample into at least four groups of monocytes, neutrophils, eosinophils and others on the basis of the fluorescent information and the two types of scattered light information. The fluorescent information is generated on the basis of intrinsic fluorescence of the eosinophils in the measurement sample.

A hemolytic agent according to a third aspect of the present invention is employed in a blood analysis method according to the second aspect of the present invention.

The hemolytic agent according to the third aspect of the present invention preferably includes a cationic surfactant.

In this case, a concentration of the cationic surfactant in a measurement sample containing a blood sample, the hemolytic agent and a diluted solution is preferably at least 0.62 mM and not more than 2.15 mM.

In the aforementioned hemolytic agent according to the third aspect, a concentration of the cationic surfactant in the hemolytic agent is preferably at least 15.5 mM and not more than 53.75 mM.

A blood analyzer according to a fourth aspect of the present invention comprises a sample preparation portion preparing a first measurement sample containing a blood sample and a hemolytic agent and a second measurement sample containing the blood sample and the same hemolytic agent as the hemolytic agent, a first light information generation portion generating fluorescent information and at least two types of scattered light information from the first measurement sample, a second light information generation portion generating either transmitted light information or scattered light information from the second measurement sample, and a control portion performing a first classification of white blood cells in the first measurement sample into at least four groups of monocytes, neutrophils, eosinophils and others on the basis of the fluorescent information and the two types of scattered light information generated by the first light information generation portion and acquiring a hemoglobin concentration in the second measurement sample on the basis of at least either the transmitted light information or the scattered light information generated by the second light information generation portion.

The aforementioned blood analyzer according to the fourth aspect preferably further comprises an electrical information generation portion generating electrical information of the second measurement sample, wherein the control portion is configured to perform a second classification of white blood cells in the second measurement sample into at least lymphocytes and others on the basis of the electrical information generated by the electrical information generation portion and classify the white blood cells in a measurement sample into at least five groups of lymphocytes, basophils, monocytes, neutrophils and eosinophils on the basis of classification results of the first classification and the second classification.

In this case, the sample preparation portion preferably further prepares a third measurement sample from the blood sample, the electrical information generation portion preferably generates electrical information of the third measurement sample, and the control portion is preferably configured to count red blood cells and platelets in the third measurement sample on the basis of the electrical information generated from the third measurement sample by the electrical information generation portion.

In the aforementioned blood analyzer according to the fourth aspect, a dilution magnification of the hemolytic agent in the second measurement sample is preferably different from a dilution magnification of the hemolytic agent in the first measurement sample.

In this case, the dilution magnification of the hemolytic agent in the second measurement sample is preferably smaller than the dilution magnification of the hemolytic agent in the first measurement sample.

In the aforementioned blood analyzer according to the fourth aspect, the sample preparation portion is preferably configured to prepare the first measurement sample by mixing the blood sample, the hemolytic agent stored in a predetermined reagent container and a predetermined quantity of diluted solution and prepare the second measurement sample by mixing the blood sample, the hemolytic agent stored in the predetermined reagent container and a quantity of the diluted solution smaller than the predetermined quantity.

In this case, the sample preparation portion is preferably configured to prepare the second measurement sample by mixing the hemolytic agent in a state of mixing the diluted solution and the blood sample.

In the aforementioned blood analyzer according to the fourth aspect, the sample preparation portion is preferably configured to prepare the second measurement sample by mixing at least the blood sample and the hemolytic agent stored in a second reagent container different from a first reagent container storing the hemolytic agent employed in the first measurement sample.

In this case, the hemolytic agent stored in the second reagent container is preferably diluted by substantially 3 times.

In the aforementioned blood analyzer according to the fourth aspect, the hemolytic agent preferably includes a cationic surfactant.

In the aforementioned blood analyzer according to the fourth aspect, the hemolytic agent preferably is free from a labeling substance. The first light information generation portion generates the fluorescent information on the basis of intrinsic fluorescence of the eosinophils in the measurement sample.

A blood analysis method according to a fifth aspect of the present invention comprises preparing a first measurement sample containing a blood sample and a hemolytic agent and a second measurement sample containing the blood sample and the same hemolytic agent as the hemolytic agent, generating fluorescent information and at least two types of scattered light information from the first measurement sample, generating at least either transmitted light information or scattered light information from the second measurement sample, classifying white blood cells in the first measurement sample into at least four groups of monocytes, neutrophils, eosinophils and others on the basis of the fluorescent information and the two types of scattered light information generated from the first measurement sample, and acquiring a hemoglobin concentration in the second measurement sample on the basis of at least either the transmitted light information or the scattered light information generated from the second measurement sample.

A hemolytic agent according to a sixth aspect of the present invention is employed in a blood analysis method according to the fifth aspect of the present invention.

The hemolytic agent according to the sixth aspect of the present invention preferably includes a cationic surfactant.

BRIEF DESCRIPTION OF THE DRAWINGS

FIG. 10 is a diagram showing a composition of a hemolytic agent employed in the blood analyzer according to the embodiment shown in FIG. 1.

FIG. 11 is a diagram showing a composition of a staining fluid for malaria detection employed in the blood analyzer according to the embodiment shown in FIG. 1.

DESCRIPTION OF THE PREFERRED EMBODIMENTS

An embodiment of the present invention is hereinafter described with reference to the drawings.

The structure of a blood analyzer 1 according to the embodiment of the present invention is now described with reference to FIGS. 1 to 11.

Figure 1:
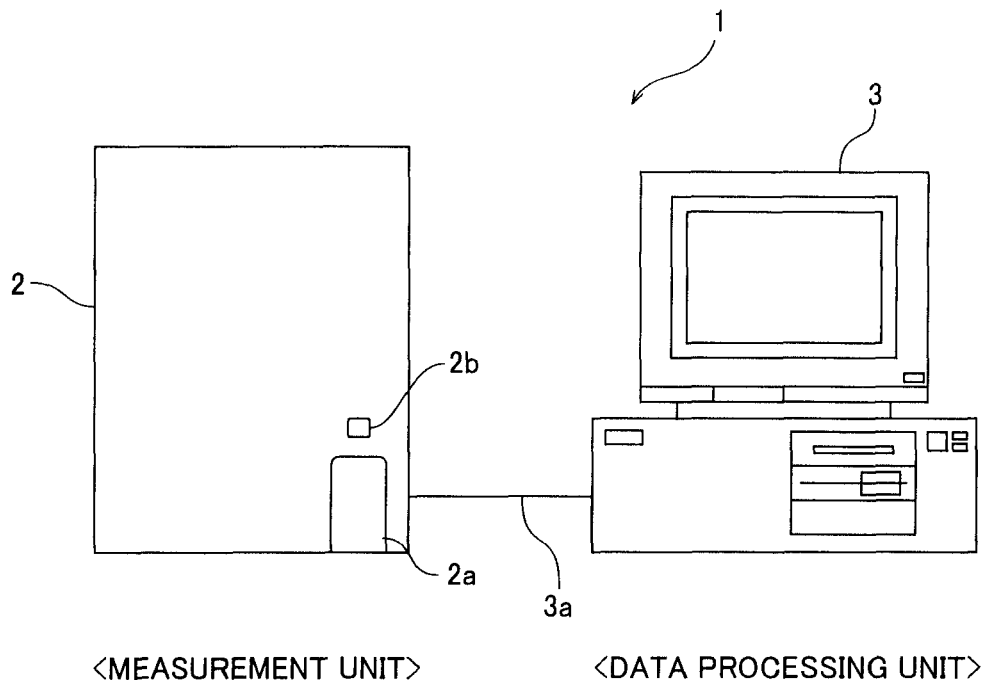
FIG. 1 is a front elevational view schematically showing the structure of a blood analyzer according to an embodiment of the present invention.

The blood analyzer 1 according to the embodiment is an apparatus employed in blood testings and mainly constituted by a measurement unit 2 and a data processing unit 3, as shown in FIG. 1. The blood analyzer 1 is set in medical facilities such as hospitals or pathology laboratories, for example. In the blood analyzer 1, the measurement unit 2 performs predetermined measurements of components contained in blood samples, and this measurement data are subjected to an analysis process when received by the data processing unit 3. The measurement unit 2 and the data processing unit 3 are so connected to each other through a data transmission cable 3a as to be capable of mutual data communication. The measurement unit 2 and the data processing unit 3 may be configured to be directly connected to each other through the data transmission cable 3a or may be connected to each other through a communication network such as a dedicated line employing a telephone line, a LAN or the Internet, for example.

Figure 2:
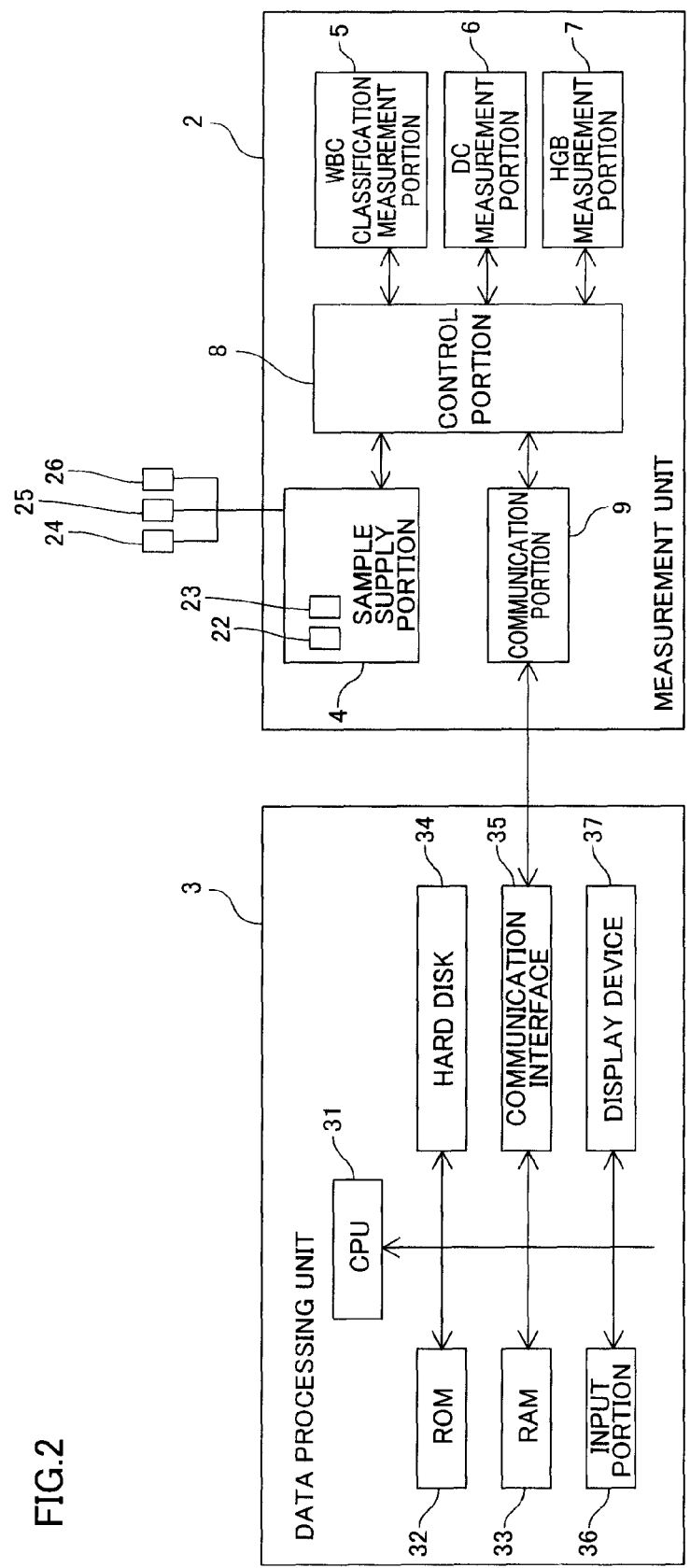
FIG. 2 is a block diagram showing the structure of the blood analyzer according to the embodiment shown in FIG. 1.
Figure 3:
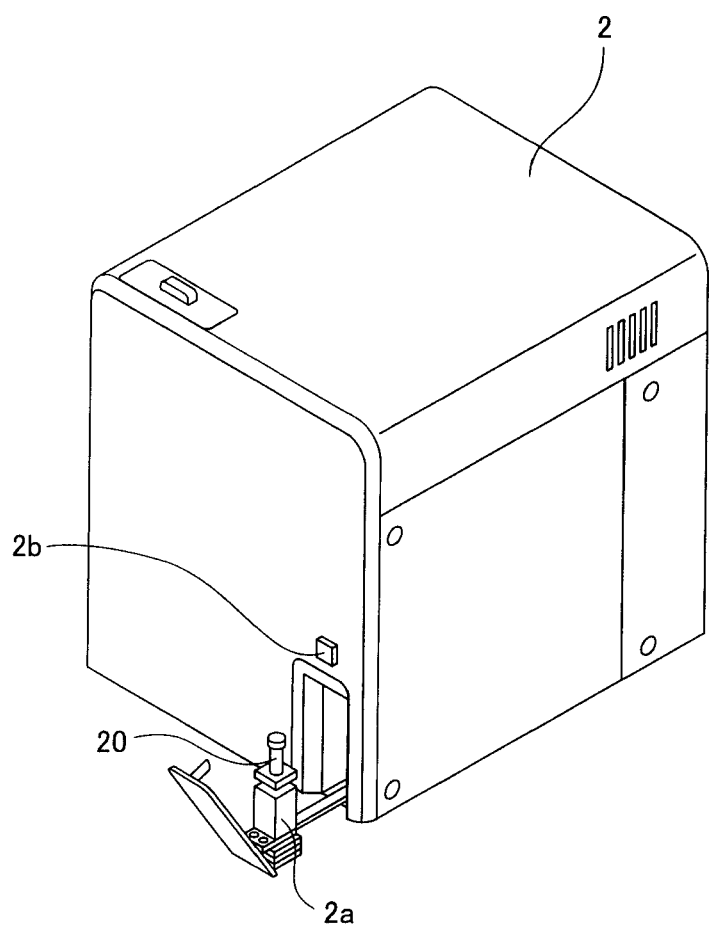
FIG. 3 is a perspective view showing a measurement unit of the blood analyzer according to the embodiment shown in FIG. 1.

The measurement unit 2 includes a sample supply portion 4, a WBC classification measurement portion 5, a DC measurement portion 6, an HGB measurement portion 7, a control portion 8 and a communication portion 9, as shown in FIG. 2. A blood collection tube set portion 2a so configured that a blood collection tube 20 storing a blood sample can be set thereon is provided at the lower right of the front of the measurement unit 2, as shown in FIG. 3. This blood collection tube set portion 2a is configured to be pushed out in a forward direction by a pressing operation of a button switch 2b provided nearby by a user. The user can set the blood collection tube 20 in a state where the blood collection tube set portion 2a is pushed out. After the blood collection tube 20 has been set, the user again presses the button switch 2b, whereby the blood collection tube set portion 2a is configured to be returned to the inside of the measurement unit 2.

Figure 4:
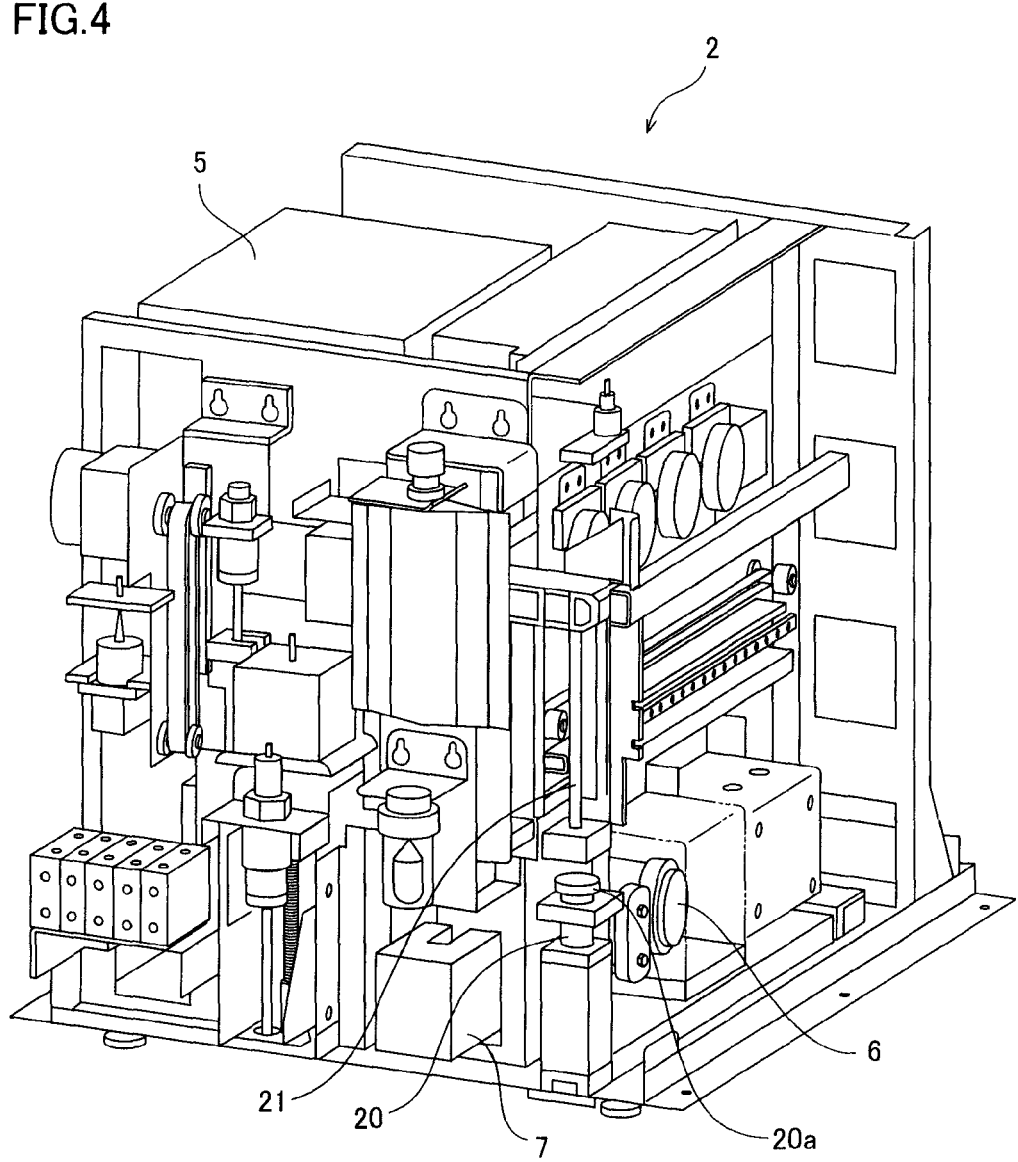
FIG. 4 is a perspective view showing the internal structure of the measurement unit of the blood analyzer according to the embodiment shown in FIG. 1.
Figure 5:
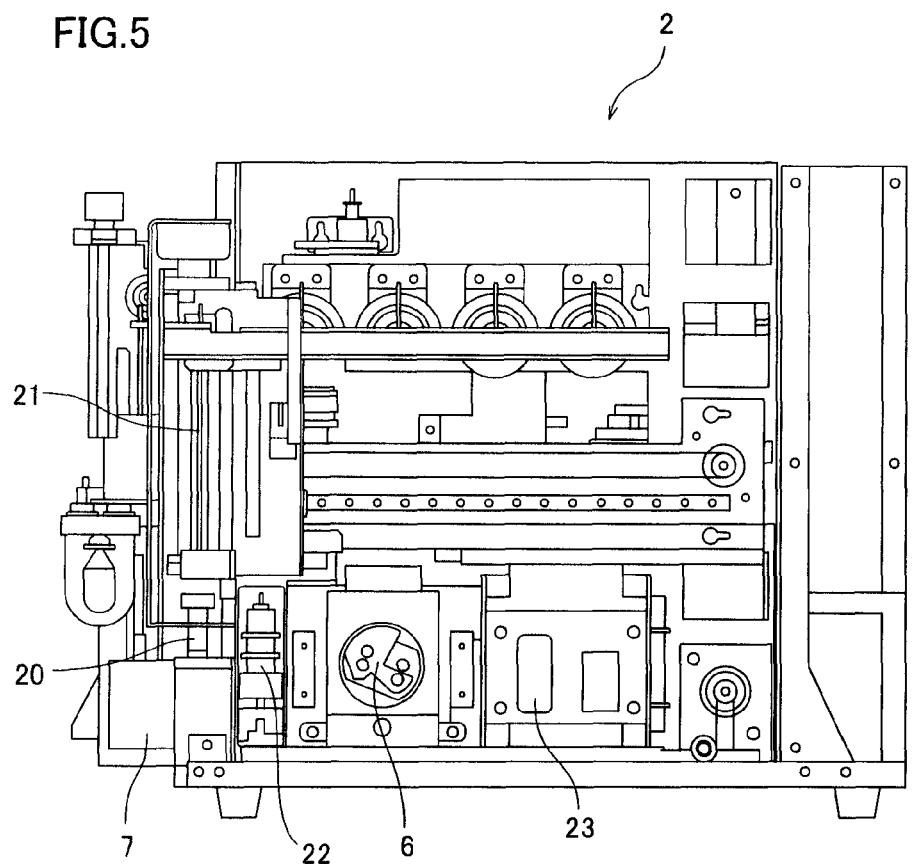
FIG. 5 is a side elevational view showing the internal structure of the measurement unit of the blood analyzer according to the embodiment shown in FIG. 1.
Figure 6:
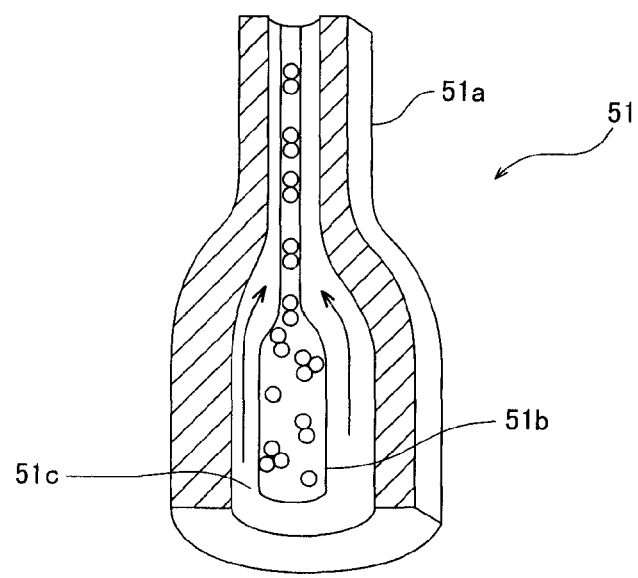
FIG. 6 is a perspective view schematically showing the structure of a flow cell provided in the measurement unit of the blood analyzer according to the embodiment shown in FIG. 1.
Figure 7:
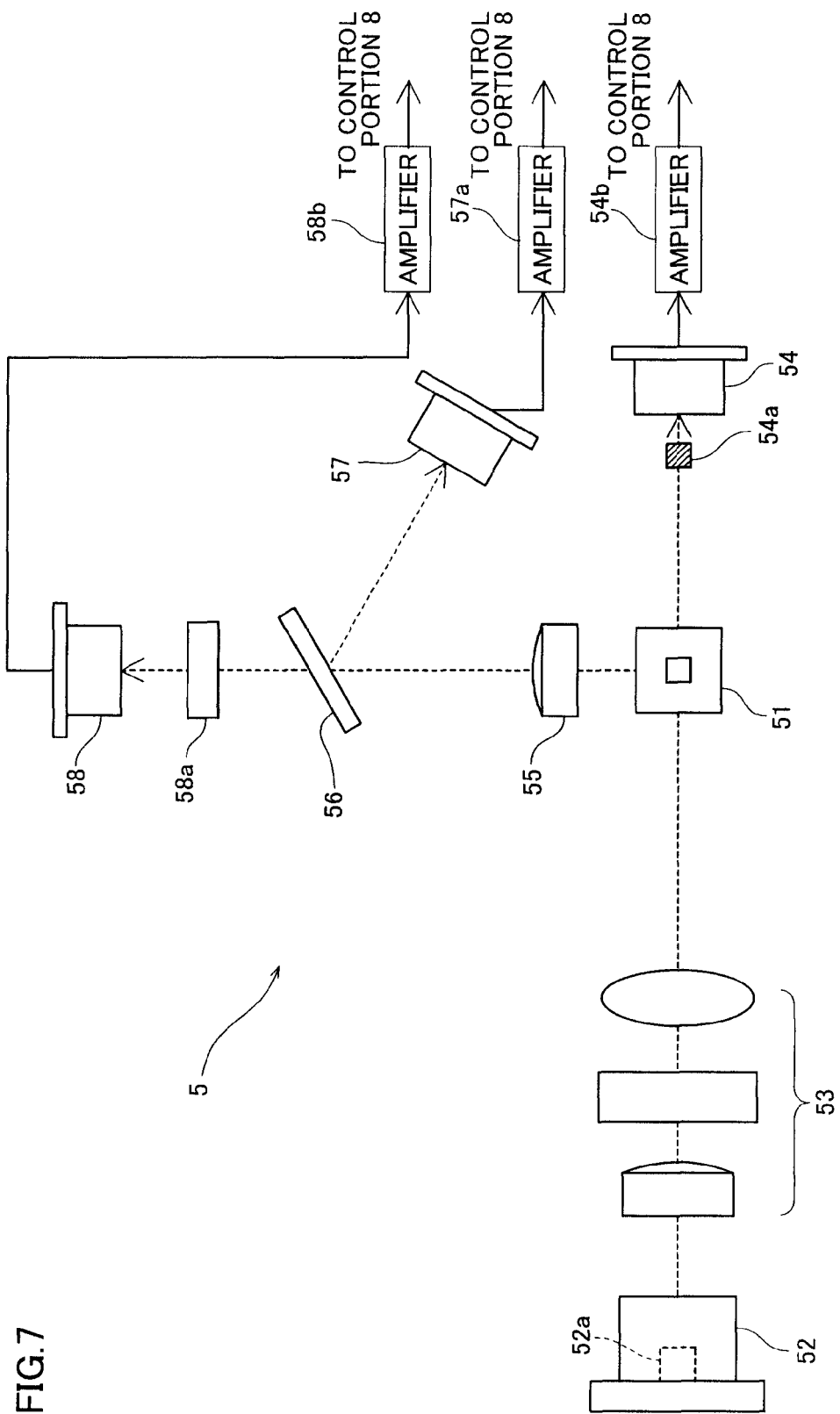
FIG. 7 is a schematic diagram showing the structure of a WBC classification measurement portion provided in the measurement unit of the blood analyzer according to the embodiment shown in FIG. 1.

A pipette 21 for suctioning measurement samples, chambers 22 and 23 (see FIG. 5) for preparation by mixing the blood sample and a reagent, and the like are provided within the measurement unit 2, as shown in FIGS. 4 and 5. The pipette 21 is formed in a shape of a tube extending vertically, and a tip thereof is sharply tapered. The pipette 21 is coupled to a syringe pump not shown in the drawings, and a predetermined quantity of liquid can be suctioned or discharged by an operation of this syringe pump. The pipette 21 is also connected to a moving mechanism and configured to be movable in vertical directions and forward and backward directions. The pipette 21 is configured to suction the blood sample stored in the blood collection tube 20 by puncturing the sharp tip into a rubber cap 20a sealing the blood collection tube 20. The pipette 21 is configured to be moved to a predetermined position by the moving mechanism and supply the blood sample to the insides of the chambers 22 and 23 after suctioning the blood sample.

The sample supply portion 4 is a flow unit having the chambers 22 and 23, a plurality of electromagnetic valves, diaphragm pumps and the like. The chamber 22 is provided for preparing a measurement sample employed in the measurement of red blood cells and platelets and the measurement of a hemoglobin concentration. The chamber 23 is provided for preparing a measurement sample employed in the measurement of white blood cells. Reagent containers are connected to the flow unit constituted by the sample supply portion 4. More specifically, a diluted solution container 24 for storing a diluted solution, a hemolytic agent container 25 for storing a hemolytic agent 100 and a staining fluid container 26 for storing a staining fluid employed in a measurement sample for detecting malaria are connected to the flow unit. Thus, the diluted solution and the hemolytic agent 100 can be supplied to the chamber 22, and the diluted solution, the hemolytic agent 100 and the staining fluid can be supplied to the chamber 23.

The WBC classification measurement portion 5 is an optical flow cytometer and provided for classifying and detecting white blood cells and detecting malaria by a flow cytometry technique employing a semiconductor laser beam. The WBC classification measurement portion 5 has a flow cell 51 (see FIG. 6) forming a fluid flow of the measurement sample. The flow cell 51 is made of a material such as quartz having a light transmission property, glass, or synthetic resin, in a shape of a tube, and is a flow path through the interior of which a sheath fluid (diluted solution) flows. This flow cell 51 is provided with an orifice 51a, the internal cavity of which has an aperture that is narrower than the other parts. The vicinity of an inlet of the orifice 51a has a double-tube structure, and an internal side of this tube part becomes a sample nozzle 51b. A cavity on an outer side of the sample nozzle 51b is a flow path 51c through which the sheath fluid (diluted solution) flows, and the sheath fluid (diluted solution) flows through the flow path 51c and is introduced into the orifice 51a. The sheath fluid (diluted solution) supplied to the flow cell 51 in this manner flows so as to surround the measurement sample discharged from the sample nozzle 51b. Then, the measurement sample flow is constricted by the orifice 51a such that particles such as white blood cells and red blood cells contained in the measurement sample are surrounded by the sheath fluid (diluted solution) and pass through the orifice 51a one by one.

A semiconductor laser light source 52 is arranged in the WBC classification measurement portion 5 so as to emit laser beam toward the orifice 51a of the flow cell 51. This semiconductor laser light source 52 has a blue-violet semiconductor laser element 52a and is configured to be capable of emitting a blue-violet laser beam having a wavelength of about 405 nm. Short-wavelength (about 405 nm) light can be easily emitted to the measurement sample by providing the blue-violet semiconductor laser element 52a in the semiconductor laser light source 52. An illumination lens system 53 constituted by a plurality of lenses is arranged between the semiconductor laser light source 52 and the flow cell 51. Parallel beams emitted from the semiconductor laser light source 52 are collected at a beam spot by the illumination lens system 53. Furthermore, a beam stopper 54a is provided on an optical axis extending linearly from the semiconductor laser light source 52 so as to be opposed to the illumination lens system 53 and with the flow cell 51 interposed therebetween, and the beam stopper 54a is configured to block direct light from the semiconductor laser light source 52.

A photodiode 54 is arranged on an optical axis on a further downstream side of the beam stopper 54a. The photodiode 54 is configured to receive scattered light of a laser beam generated by the measurement sample flowing through the flow cell 51. More specifically, among light advancing along the optical axis extending linearly from the semiconductor laser light source 52, the direct light of the semiconductor laser light source 52 is blocked by the beam stopper 54a, and hence the photodiode 54 is configured to basically receive only scattered light (hereinafter referred to as forward scattered light) advancing along the optical axis direction. The forward scattered light emitted from the flow cell 51 is subjected to photoelectric conversion by the photodiode 54, and electrical signals (hereinafter referred to as forward scattered light signals) generated by this conversion are transmitted to an amplifier 54b. The amplifier 54b is configured to amplify the transmitted forward scattered light signals and output the amplified forward scattered light signals to a control portion 8.

Furthermore, a side collective lens 55 is arranged at a side of the flow cell 51, in a direction perpendicular to the optical axis extending linearly from the semiconductor laser light source 52 to the photodiode 54, and this side collective lens 55 is configured to collect lateral light (light emitted in a direction intersecting with the aforementioned optical axis) generated when emitting a laser beam to blood cells passing through the flow cell 51. A dichroic mirror 56 is provided on a downstream side of the side collective lens 55, and the dichroic mirror 56 is configured to divide signal light transmitted from the side collective lens 55 into a scattered light component and a fluorescent light component. A side scattered light photoreceptor photodiode 57 is provided at a side (a direction intersecting with a direction of an optical axis connecting the side collective lens 55 and the dichroic mirror 56) of the dichroic mirror 56, and an optical filter 58a and avalanche photodiode 58 are provided on an optical axis on a downstream side of the dichroic mirror 56. The side scattered light component separated by the dichroic mirror 56 is subjected to photoelectric conversion by the photodiode 57, and electrical signals (hereinafter referred to as side scattered light signals) generated by this conversion are transmitted to an amplifier 57a. The amplifier 57a is configured to amplify the transmitted side scattered light signals and output the amplified side scattered light signals to the control portion 8.

Furthermore, the side fluorescent light component is subjected to wavelength selection by the optical filter 58a, and subsequent photoelectric conversion by the avalanche photodiode 58, and electrical signals (side fluorescent light signals) generated by this are transmitted to an amplifier 58b. The amplifier 58b is configured to amplify the transmitted side fluorescent light signals and output the amplified side fluorescent light signals to the control portion 8.

Figure 8:
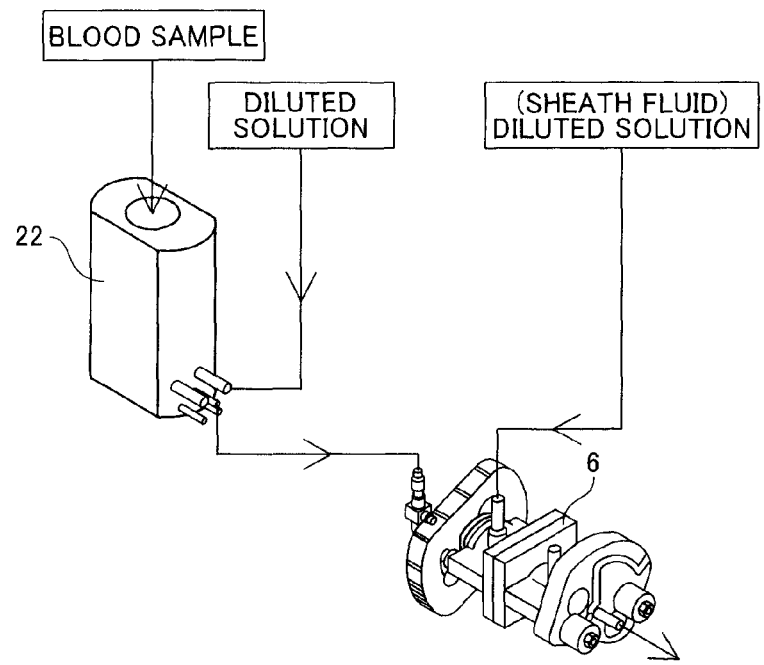
FIG. 8 is a perspective view schematically showing the structure of a DC measurement portion provided in the measurement unit of the blood analyzer according to the embodiment shown in FIG. 1.

The DC measurement portion 6 is configured to be capable of measuring a red blood cell count (RBC) and a platelet count (PLT) by a sheath flow DC detection method. The DC measurement portion 6 is configured to be capable of acquiring measurement data for calculating a hematocrit value (HCT) by a red-blood-cell pulse height detection method. Further, the DC measurement portion 6 is employed in detection of a white blood cell count (WBC) for calculating a lymphocyte ratio. The DC measurement portion 6 is commonly employed in measurement of a red blood cell count and a platelet count, acquisition of the measurement data for calculating a hematocrit value (HCT) and detection of a white blood cell count (WBC) for calculating a lymphocyte ratio in this manner, whereby it is not necessary to provide separate measurement portions for measuring these items. The DC measurement portion 6 has a flow cell, and the measurement sample is transferred from the chamber 22 to the flow cell. When measuring a red blood cell count and a platelet count, for example, a measurement sample prepared by mixing the blood sample and the diluted solution in the chamber 22, along with the sheath fluid (diluted solution), is transferred from the sample supply portion 4 to the flow cell, as shown in FIG. 8. A fluid flow in a state where the measurement sample is surrounded by the sheath fluid (diluted solution) is formed in the flow cell.

Figure 9:
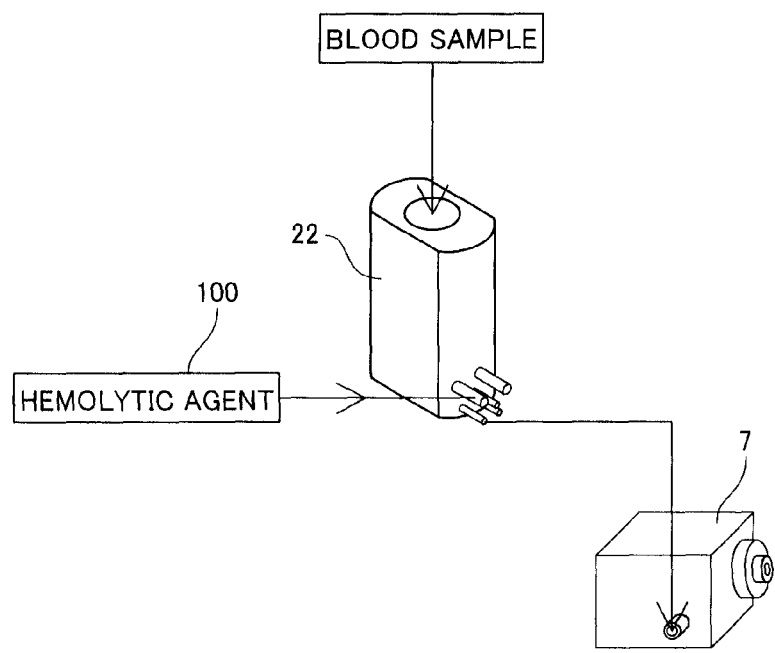
FIG. 9 is a perspective view schematically showing the structure of an HGB measurement portion provided in the measurement unit of the blood analyzer according to the embodiment shown in FIG. 1.
Figure 12:
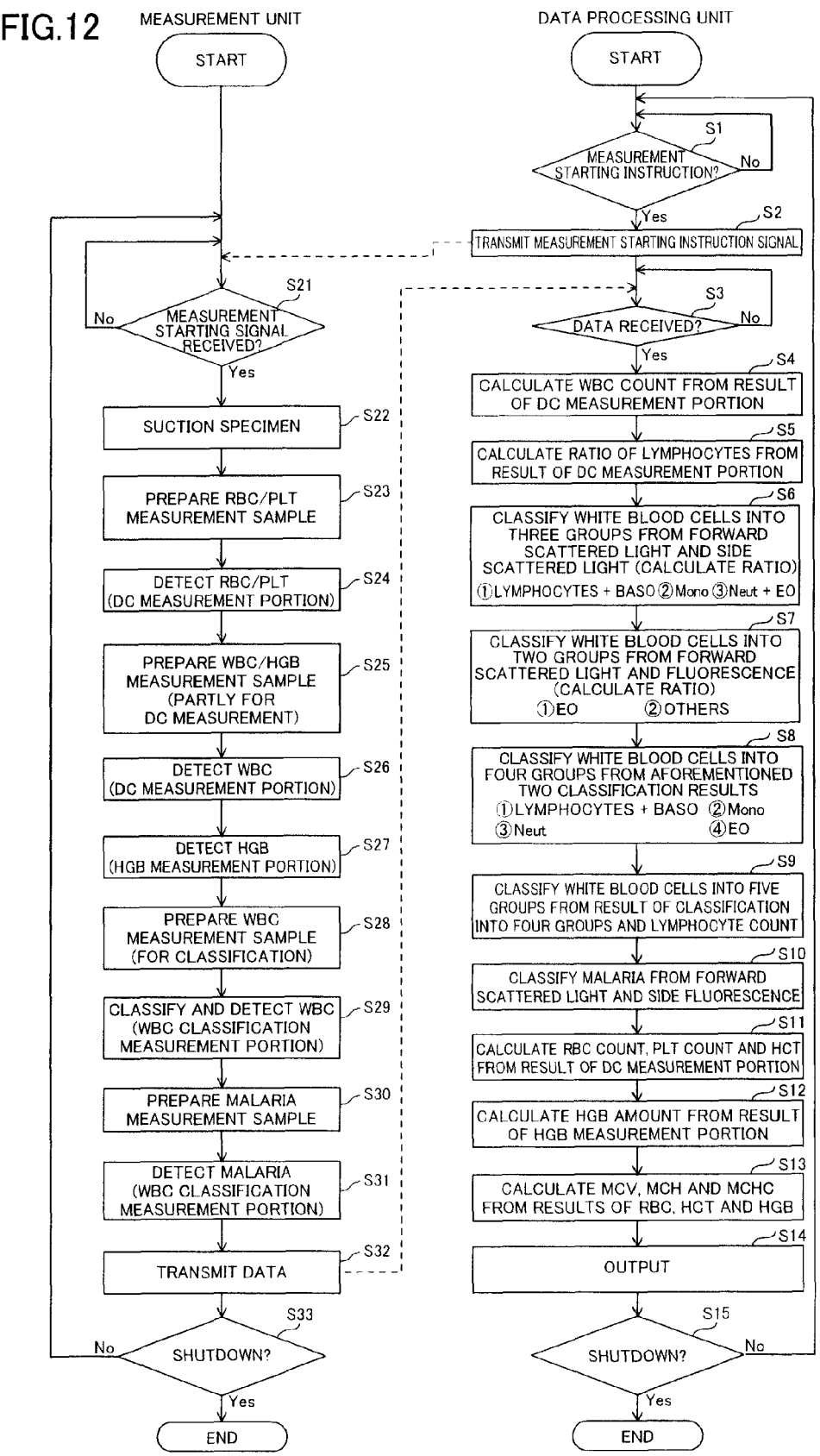
FIG. 12 is a flow chart showing sample analysis processing in the blood analyzer according to the embodiment shown in FIG. 1.

The HGB measurement portion 7 is configured to measure the amount of hemoglobin (HGB) by a methemoglobin method. The HGB measurement portion 7 has a cell storing a dilute sample, as shown in FIG. 9, and the measurement sample is transferred from the chamber 22 to this cell. The HGB measurement portion 7 has a light-emitting diode emitting light having a wavelength of about 555 nm and is configured to measure absorbance of the measurement sample by emitting the light from the light-emitting diode to the measurement sample in the aforementioned cell. When measuring hemoglobin, a measurement sample is prepared by mixing the blood sample, the diluted solution and the hemolytic agent 100 in the chamber 22.

The control portion 8 is constituted by a CPU, a ROM, a RAM, etc. and configured to control an operation of each part of the measurement unit 2.

The communication portion 9 is an RS-232C interface, a USB interface or an Ethernet (registered trademark) interface, for example and is configured to be capable of sending/receiving data to/from the data processing unit 3.

The data processing unit 3 is constituted by a computer comprising a CPU 31, a ROM 32, a RAM 33, a hard disk 34, a communication interface 35, an input portion 36 such as a keyboard and a mouse, and a display device 37, as shown in FIG. 2. An operating system, and an application program for analyzing the measurement data received from the measurement unit 2 are installed on the hard disk 34 of the data processing unit 3.

According to this embodiment, the CPU 31 of the data processing unit 3 is configured to analyze the measurement data and calculate a white blood cell count (WBC), a red blood cell count (RBC), a hemoglobin amount (HGB), a hematocrit value (HCT), a mean red blood cell volume (MCV), a mean red blood cell hemoglobin amount (MCH), a mean red blood cell hemoglobin concentration (MCHC), a platelet count (PLT) by executing this application program. Further, the CPU 31 is configured to prepare a scattergram employing the forward scattered light signals, the side scattered light signals and the side fluorescent light signals and classify the white blood cells into five groups of neutrophils (Neut), lymphocytes, monocytes (Mono), eosinophils (EO), and basophils (BASO).

The communication interface 35 is an RS-232C interface, a USB interface or an Ethernet (registered trademark) interface, for example and is configured to be capable of sending/receiving data to/from the measurement unit 2.

The hemolytic agent 100 according to this embodiment includes a cationic surfactant (lauryl trimethyl ammonium chloride; 34.1 mM, stearyl trimethyl ammonium chloride; 1.7 mM) but is free from a labeling substance, as shown in FIG. 10. The labeling substance is a substance which is selectively provided to a target cell under measurement and becomes a label for measurement, and a fluorescent dye staining nucleic acid of the target cell under measurement corresponds to the labeling substance, for example. This hemolytic agent 100 has a property in that hemoglobin in the blood is inverted to methemoglobin. As described later, each measurement sample employed in each measurement has a different dilution magnification of the hemolytic agent 100 and a different dilution magnification of the blood sample. The cationic surfactant is employed as described above, whereby white blood cells in the measurement sample can be classified into four groups and a hemoglobin concentration in the measurement sample can be acquired by simply varying the dilution magnification without employing more than one type of a hemolytic agent. The staining fluid contains a fluorescent dye (Hoechst 34580 of Invitrogen, for example) having a structure of a chemical formula shown in FIG. 11 and one of a nonionic surfactant group shown in FIG. 11. This fluorescent dye can be excited by the blue-violet laser beam (the wavelength is about 405 nm) emitted from the semiconductor laser light source 52.

Next, sample analysis processing in the blood analyzer 1 according to the embodiment of the present invention is described with reference to FIGS. 12 to 17.

First, when the blood analyzer 1 is started, the application program or the like is initialized, and thereafter the CPU 31 of the data processing unit 3 determines whether or not a measurement starting instruction from a user has been received at a step S1, and this determination is repeated until the instruction has been received. When the measurement starting instruction has been received, a measurement starting instruction signal is transmitted from the data processing unit 3 to the measurement unit 2 at a step S2.

Then, the control portion 8 of the measurement unit 2 determines whether or not the measurement starting instruction signal has been received at a step S21, and this determination is repeated until the signal has been received. When the measurement unit 2 has received the measurement starting instruction signal, the blood sample is suctioned from the blood collection tube 20 set on the blood collection tube set portion 2a by the pipette 21 at a step S22.

Figure 13:
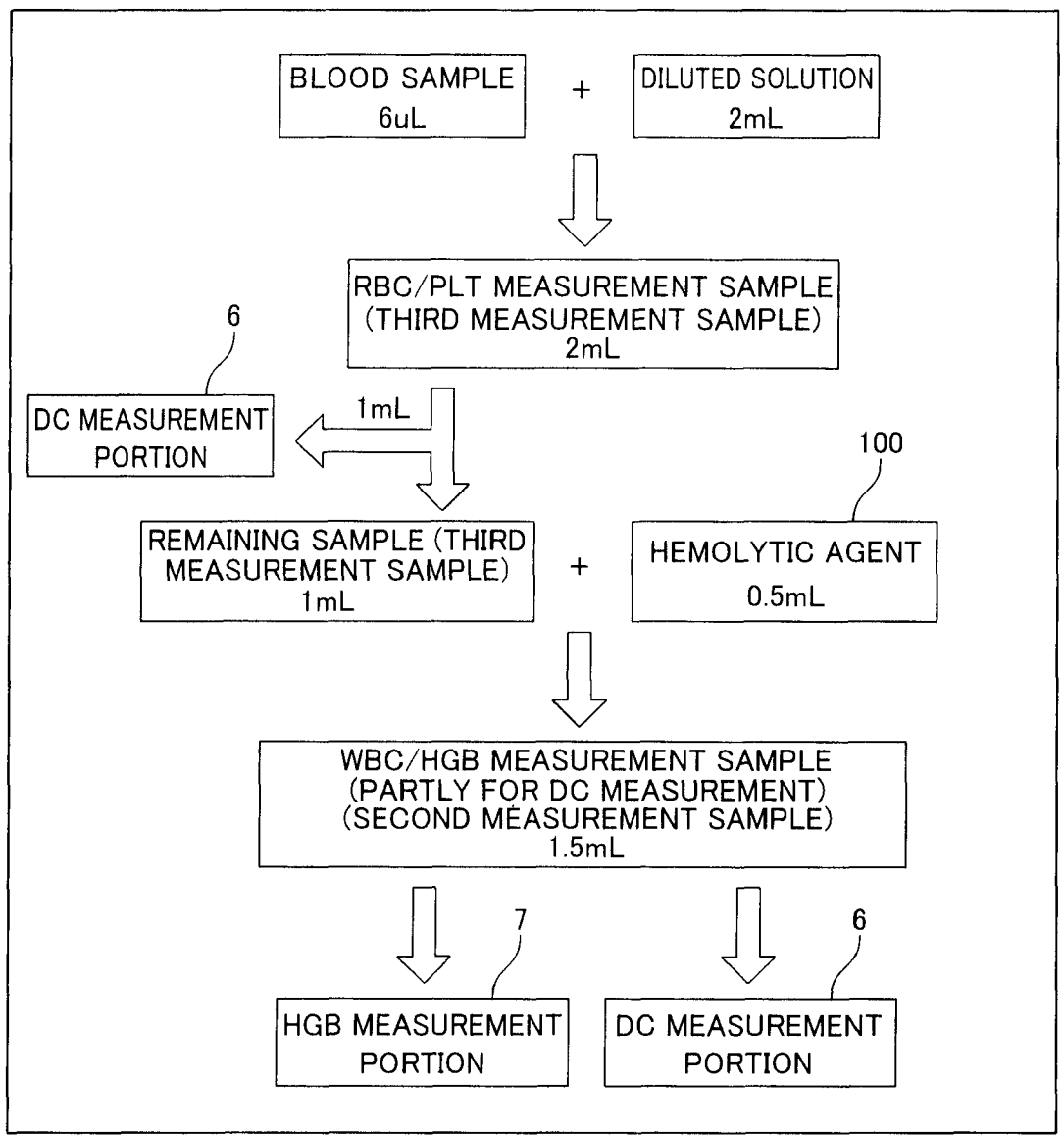
FIG. 13 is a diagram for illustrating a step of preparing a third measurement sample and a second measurement sample employed in the blood analyzer according to the embodiment shown in FIG. 1.

At a step S23, an RBC/PLT measurement sample (hereinafter referred to as the third measurement sample) is prepared by the sample supply portion 4. More specifically, a predetermined quantity (2.0 mL, for example) of the diluted solution from the diluted solution container 24 and a predetermined quantity (6 μL, for example) of the blood sample suctioned from the blood collection tube 20 by the pipette 21 are supplied to the chamber 22 and stirred, as shown in FIG. 13. Thus, a predetermined quantity (2.0 mL, for example) of the third measurement sample is prepared. Thereafter, a part (1 mL, for example) of the third measurement sample in the chamber 22, along with the sheath fluid (diluted solution), is transferred to the DC measurement portion 6 and the DC measurement portion 6 detects the RBC and the PLT of the third measurement sample at a step S24.

Then, at a step S25, a WBC/HGB measurement sample (partly for DC detection) (hereinafter referred to as the second measurement sample) is prepared by the sample supply portion 4. More specifically, a predetermined quantity (0.5 mL, for example) of the hemolytic agent 100 is supplied from the hemolytic agent container 25 to the chamber 22 in which a predetermined quantity (1 mL, for example) of the third measurement sample remains and stirred, as shown in FIG. 13. In other words, after the blood sample and the diluted solution are mixed in the chamber 22, the hemolytic agent 100 is mixed to prepare the second measurement sample. Thus, the hemolytic agent is mixed with the blood sample in a state of being diluted with the diluted solution, and hence the blood sample can be inhibited from being mixed with the hemolytic agent having a concentration higher than a desired concentration. In this way, the second measurement sample in which the hemolytic agent 100 is diluted by 3 times (hemolytic agent/diluted solution=1/2) and the blood sample is diluted by 500 times is prepared. Thus, the red blood cells are hemolyzed, and the hemoglobin is inverted to methemoglobin. The dilution magnification (3 times) of the hemolytic agent 100 in the second measurement sample is rendered smaller than a dilution magnification (25 times) of the hemolytic agent 100 in the first measurement sample described later, whereby the red blood cells in the measurement sample can be reliably hemolyzed, and hence the hemoglobin concentration can be accurately acquired. Thereafter, at a step S26, the second measurement sample in the chamber 22 is transferred to the DC measurement portion 6, and the WBC in the second measurement sample is measured. At a step S27, the second measurement sample is transferred to the HGB measurement portion 7, and the HGB of the second measurement sample is detected.

At a step S28, a WBC measurement sample (for classification) (hereinafter referred to as the first measurement sample) is prepared by the sample supply portion 4. More specifically, a predetermined quantity (1 mL, for example) of a diluted hemolytic agent obtained by diluting the same hemolytic agent 100 as that contained in the aforementioned second measurement sample by 25 times (hemolytic agent/diluted solution=1/24) and a predetermined quantity (10 μL, for example) of the blood sample suctioned from the blood collection tube 20 are supplied to the chamber 23 and stirred. Thus, the first measurement sample in which the blood sample is diluted by 100 times is prepared. Thus, the first measurement sample and the second measurement sample can be prepared employing the common hemolytic agent 100 stored in the hemolytic agent container 25. Thereafter, the first measurement sample in the chamber 23, along with the sheath fluid (diluted solution), is transferred to the WBC classification measurement portion 5 and the WBC classification measurement portion 5 detects the WBC in the first measurement sample at a step S29.

Then, at a step S30, a malaria measurement sample (hereinafter referred to as the fourth measurement sample) is prepared by the sample supply portion 4. More specifically, a predetermined quantity (1 mL, for example) of a diluted hemolytic agent obtained by diluting the hemolytic agent 100 by 9 times (hemolytic agent/diluted solution=1/8), a predetermined quantity (10 μL, for example) of the blood sample suctioned from the blood collection tube 20 and a predetermined quantity (10 μL, for example) of the staining fluid from the staining fluid container 26 are supplied to the chamber 23 and stirred. Thus, the fourth measurement sample in which the blood sample is diluted by 100 times is prepared. Thereafter, the fourth measurement sample in the chamber 23, along with the sheath fluid (diluted solution), is transferred to the WBC classification measurement portion 5 and the WBC classification measurement portion 5 detects malaria of the fourth measurement sample at a step S31. At a step S32, measurement data obtained by measurement in each detection portion is transmitted from the measurement unit 2 to the data processing unit 3.

Figure 14:
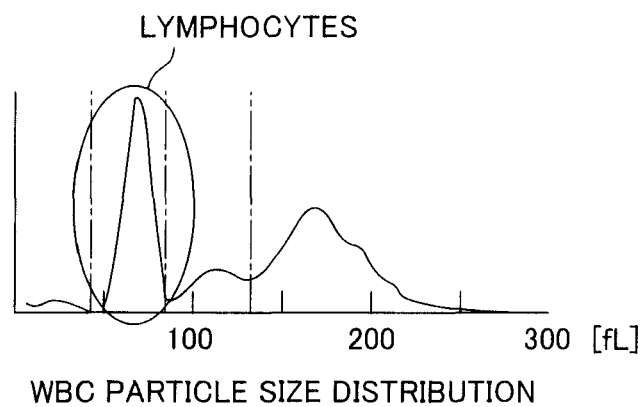
FIG. 14 is a particle size distribution chart of white blood cells prepared in the blood analyzer according to the embodiment shown in FIG. 1.

The data processing unit 3 determines whether or not the measurement data transmitted from the measurement unit 2 has been received at a step S3, and this determination is repeated until the measurement data has been received. When the measurement data has been received, at a step S4, the CPU 31 calculates the white blood cell count (WBC) on the basis of the measurement data obtained by the WBC detection, measured at the step S26. At a step S5, the CPU 31 prepares a particle size distribution chart of the white blood cells on the basis of the measurement data obtained by the WBC detection, as shown in FIG. 14 and calculates the ratio of the lymphocytes to the white blood cell count (WBC). The lymphocyte appears as a first peak (group) from the left in the particle size distribution chart.

Figure 15:
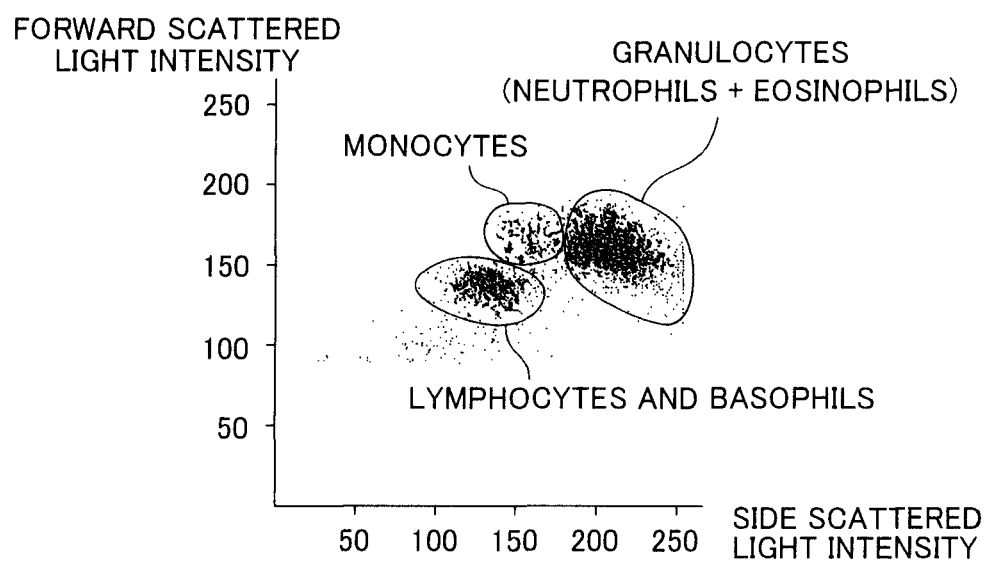
FIG. 15 is a scattergram for classification of white blood cells prepared in the blood analyzer according to the embodiment shown in FIG. 1.
Figure 22:
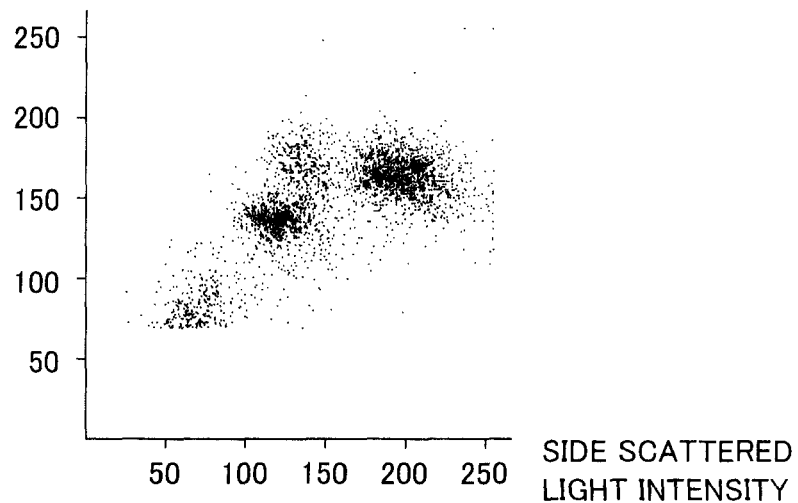
FIG. 22 is a diagram showing an experimental result when employing the hemolytic agent shown in FIG. 10 in the blood analyzer according to the embodiment shown in FIG. 1.

Then, at a step S6, the CPU 31 classifies the white blood cells into three groups of a group of lymphocytes and basophils, monocytes and granulocytes (a group of neutrophils and eosinophils) on the basis of the measurement data obtained by the WBC classification and detection, measured at the step S29. More specifically, the CPU 31 prepares a scattergram, employing the forward scattered light signals and the side scattered light signals, as shown in FIG. 15 and calculates ratios of a group of lymphocytes and basophils, monocytes and granulocytes (a group of neutrophils and eosinophils) to the white blood cell count (WBC) from this scattergram. FIG. 22 shows a scattergram by a forward scattered light signal and a side scattered light signal obtained by measuring a blood sample actually collected from a subject employing the hemolytic agent 100 (see FIG. 10) in this embodiment. As shown in FIG. 22, it is also understood from an actual measurement result that the white blood cells can be classified into three groups of a group of lymphocytes and basophils, monocytes and granulocytes (a group of neutrophils and eosinophils) on the scattergram.

Figure 16:
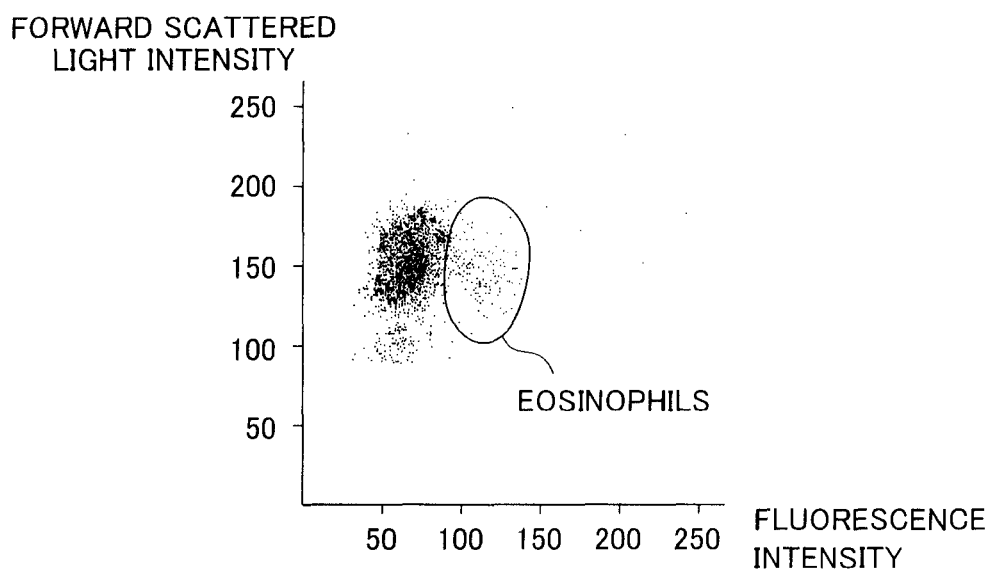
FIG. 16 is a scattergram for classification of white blood cells prepared in the blood analyzer according to the embodiment shown in FIG. 1.
Figure 23:
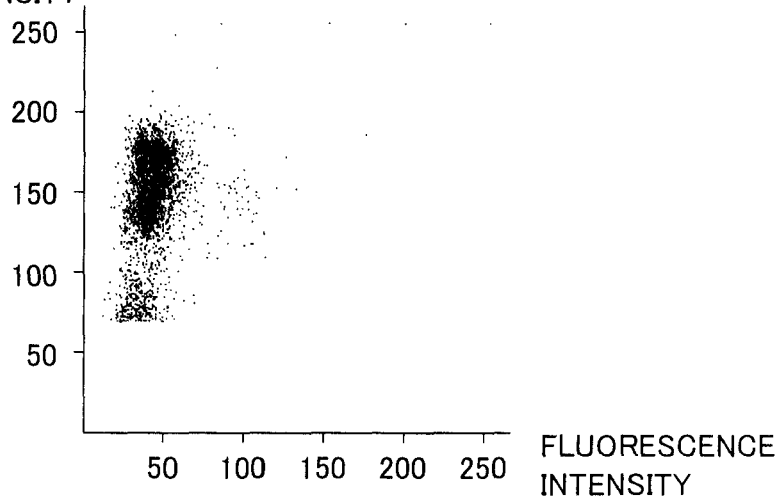
FIG. 23 is a diagram showing an experimental result when employing the hemolytic agent shown in FIG. 10 in the blood analyzer according to the embodiment shown in FIG. 1.
Figure 24:
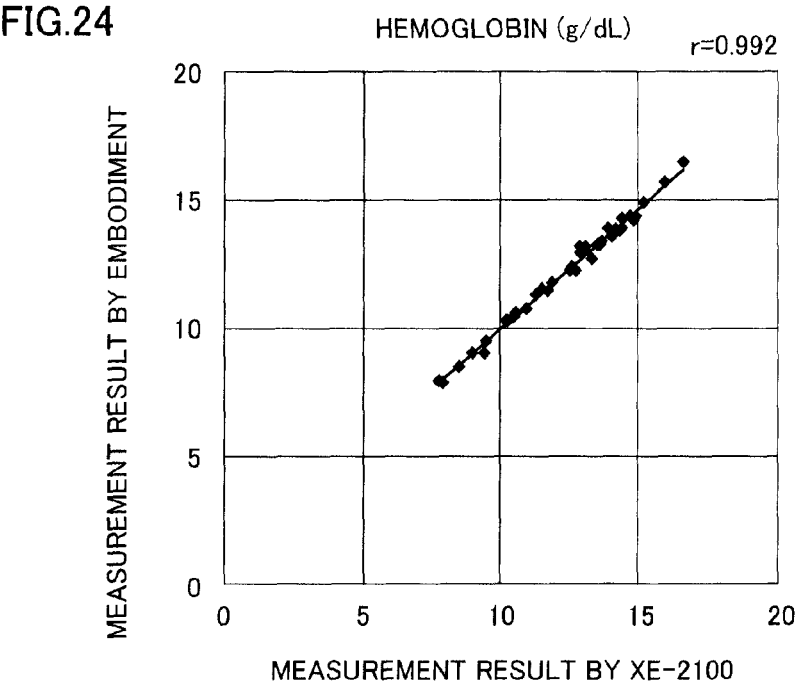
FIG. 24 is a correlation diagram of hemoglobin showing a correlation between a measurement result of a specimen in each of a plurality of blood samples obtained by a method (employing a reagent similar to that described in the embodiment described later) described in the embodiment described later and a measurement result of the same specimen in each of the plurality of blood samples obtained by a multiparameter automated hematology analyzer Model XE-2100 (SYSMEX CORPORATION).
Figure 25:
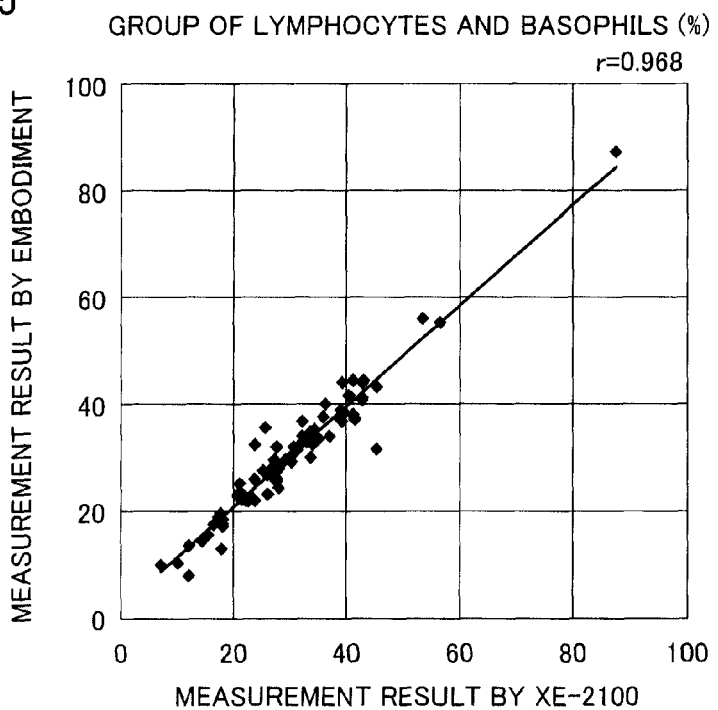
FIG. 25 is a correlation diagram of a group of lymphocytes and basophils showing a correlation between a measurement result of a specimen in each of the plurality of blood samples obtained by the method (employing a reagent similar to that described in the embodiment described later) described in the embodiment described later and a measurement result of the same specimen in each of the plurality of blood samples obtained by the multiparameter automated hematology analyzer Model XE-2100 (SYSMEX CORPORATION).
Figure 26:
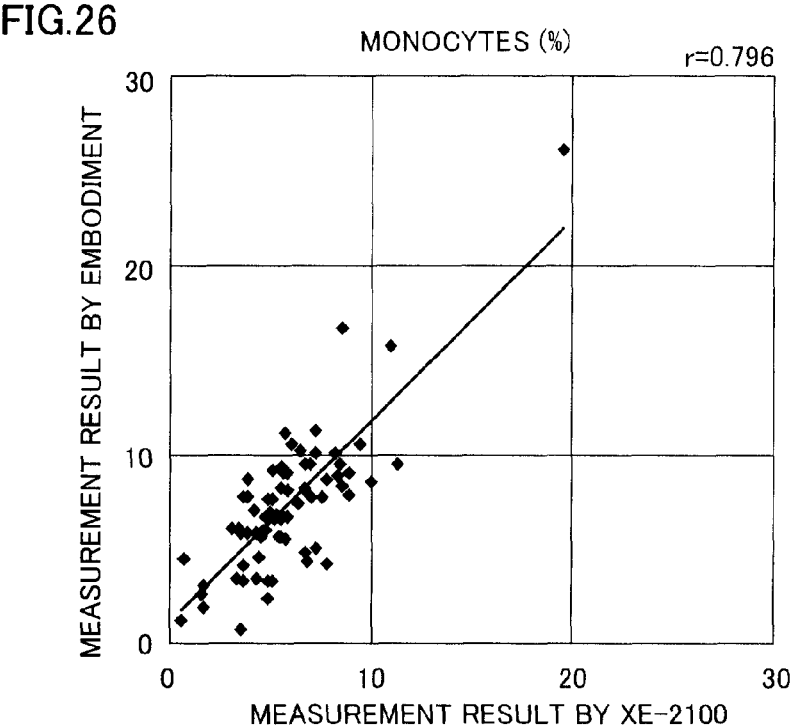
FIG. 26 is a correlation diagram of monocytes showing a correlation between a measurement result of a specimen in each of the plurality of blood samples obtained by the method (employing a reagent similar to that described in the embodiment described later) described in the embodiment described later and a measurement result of the same specimen in each of the plurality of blood samples obtained by the multiparameter automated hematology analyzer Model XE-2100 (SYSMEX CORPORATION).
Figure 27:
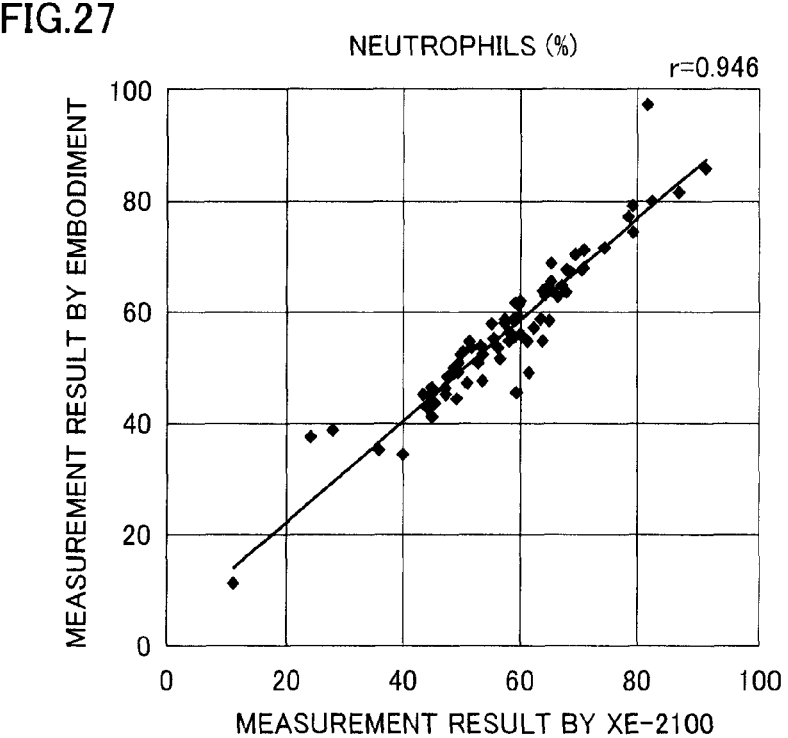
FIG. 27 is a correlation diagram of neutrophils showing a correlation between a measurement result of a specimen in each of the plurality of blood samples obtained by the method (employing a reagent similar to that described in the embodiment described later) described in the embodiment described later and a measurement result of the same specimen in each of the plurality of blood samples obtained by the multiparameter automated hematology analyzer Model XE-2100 (SYSMEX CORPORATION).
Figure 28:
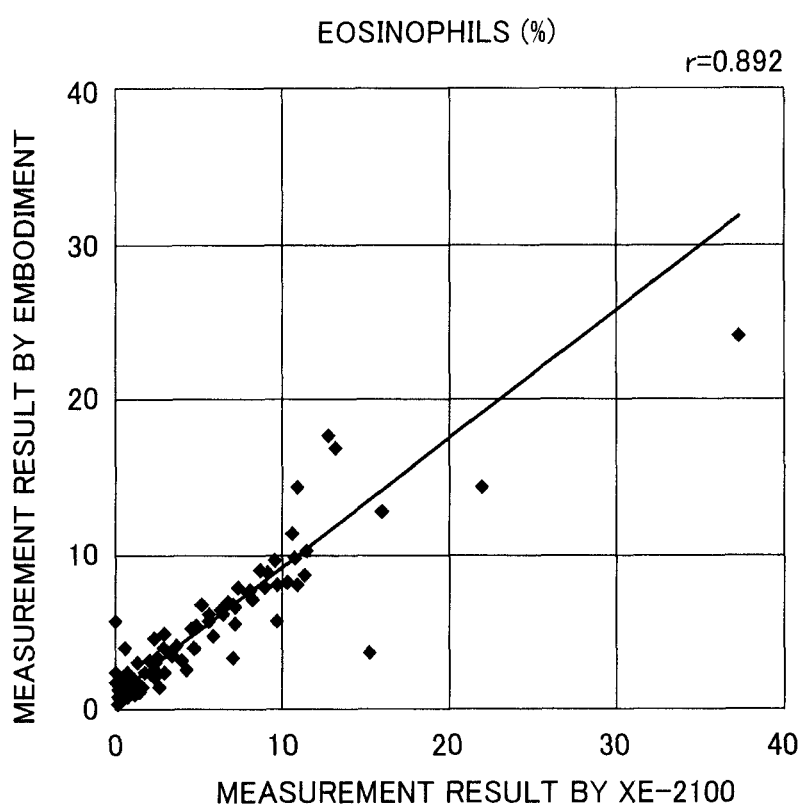
FIG. 28 is a correlation diagram of eosinophils showing a correlation between a measurement result of a specimen in each of the plurality of blood samples obtained by the method (employing a reagent similar to that described in the embodiment described later) described in the embodiment described later and a measurement result of the same specimen in each of the plurality of blood samples obtained by the multiparameter automated hematology analyzer Model XE-2100 (SYSMEX CORPORATION).

At a step S7, the CPU 31 classifies the white blood cells into two groups of eosinophils and the others on the basis of the measurement data obtained by the WBC classification and detection. More specifically, the CPU 31 prepares a scattergram, employing the forward scattered light signals and the side fluorescent light signals, as shown in FIG. 16 and calculates a ratio of the eosinophils to the white blood cell count (WBC) from this scattergram. These side fluorescent light signals are based on intrinsic fluorescence of the white blood cells excited by the blue-violet semiconductor laser beam (the wavelength is about 405 nm) emitted from the semiconductor laser light source 52, and the eosinophils have a stronger fluorescence intensity than the others in the white blood cells. Thus, according to this embodiment, the white blood cells can be classified into the eosinophils and the others without employing a labeling substance. The CPU 31 can also calculate the ratio of the eosinophils to the white blood cell count (WBC) from a scattergram obtained by employing the side scattered light signals and the side fluorescent light signals. FIG. 23 shows a scattergram by the forward scattered light signal and a side fluorescent light signal obtained by measuring the blood sample actually collected from the subject employing the hemolytic agent 100 (see FIG. 10) in this embodiment. As shown in FIG. 23, it is also understood from an actual measurement result that the white blood cells can be classified into the eosinophils and the others on the scattergram.

Thereafter, at a step S8, the CPU 31 calculates a ratio of the neutrophils to the white blood cell count (WBC) by subtracting the ratio of the eosinophils calculated at the step S7 from the ratio of the granulocytes (a group of neutrophils and eosinophils) calculated at the step S6. Thus, the white blood cells are classified into four groups of the group of lymphocytes and basophils, the monocytes, the neutrophils and the eosinophils. At a step S9, the CPU 31 calculates a ratio of the basophils to the white blood cell count (WBC) by subtracting the ratio of the lymphocytes calculated at the step S5 from the ratio of the group of lymphocytes and basophils. Thus, the white blood cells are classified into five groups of the lymphocytes, the basophils, the monocytes, the neutrophils and the eosinophils.

Figure 17:
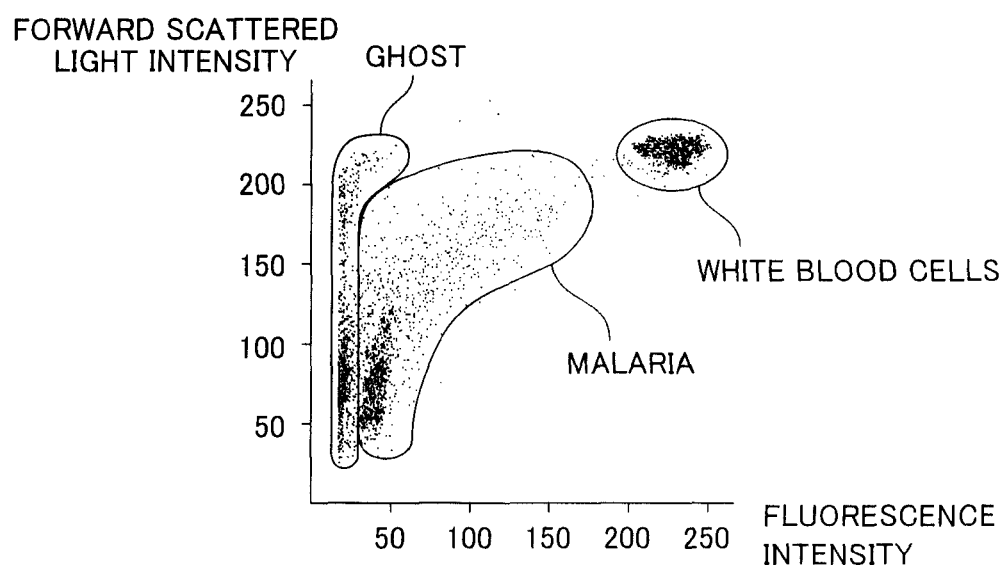
FIG. 17 is a scattergram for classification of malaria prepared in the blood analyzer according to the embodiment shown in FIG. 1.

At a step S10, the CPU 31 separates the red blood cells infected by malarial parasite from the others on the basis of the measurement data obtained by the malaria detection, measured at the step S31. More specifically, the CPU 31 prepares a scattergram, employing the forward scattered light signals and the side fluorescent light signals, as shown in FIG. 17 and separates the red blood cells infected by malarial parasite from the others from this scattergram. Thus, the presence of malaria infection can be determined.

Then, at a step S11, the CPU 31 calculates the red blood cell count (RBC), the platelet count (PLT) and the hematocrit value (HCT) on the basis of the measurement data obtained by the RBC/PLT detection, measured at the step S24.

According to this embodiment, at a step S12, the CPU 31 calculates the amount of the hemoglobin (HGB) on the basis of the measurement data obtained by the HGB detection, measured at the step S27. In other words, the hemoglobin concentration is calculated on the basis of the absorbance obtained by HGB detection employing an SLS hemoglobin method.

Thereafter, at a step S13, the CPU 31 calculates the mean red blood cell volume (MCV), the mean red blood cell hemoglobin amount (MCH) and the mean red blood cell hemoglobin concentration (MCHC) from the red blood cell count (RBC), the hematocrit value (HCT) and the amount of the hemoglobin (HGB).

The formula for calculating each value is expressed by the following formulas (1) to (3):

$$MCV = (HCT/RBC) \times 1000 \qquad (1)$$

In the aforementioned formula (1), MCV represents a mean red blood cell volume (fL), HCT represents a hematocrit value (%) and RBC represents a red blood cell count ($\times 10^4/\mu L$).

$$MCH = (HGB/RBC) \times 1000 \qquad (2)$$

In the aforementioned formula (2), MCH represents a mean red blood cell hemoglobin amount (pg), HGB represents the amount of hemoglobin (g/dL) and RBC represents a red blood cell count ($\times 10^4/\mu L$).

$$MCHC = (HGB/HCT) \times 100 \qquad (3)$$

In the aforementioned formula (3), MCHC represents a mean red blood cell hemoglobin concentration (g/dL), HGB represents the amount of hemoglobin (g/dL) and HCT represents a hematocrit value (%).

At a step S14, calculation results of the white blood cell count (WBC), the red blood cell count (RBC), the amount of the hemoglobin (HGB), the hematocrit value (HCT), the mean red blood cell volume (MCV), the mean red blood cell hemoglobin amount (MCH), the mean red blood cell hemoglobin concentration (MCHC) and the platelet count (PLT) calculated as described above are output to the display device 37. Further, the ratios of the neutrophils, the lymphocytes, the monocytes, the eosinophils and the basophils to the white blood cell count (WBC) are output to the display device 37, and the result of detection of malaria is also output. In addition to the ratio of each blood cell to the white blood cell count (WBC), the white blood cell count (WBC) and the neutrophil count, the lymphocyte count, the monocyte count, the eosinophil count and the basophil count calculated on the basis of the ratio of each blood cell are output.

Thereafter, at a step S15, the presence of a shutdown instruction from the user is determined, and when the shutdown instruction has not been received, the CPU 31 moves to the step S1. When the shutdown instruction has been received, an operation of the data processing unit 3 of the sample analysis processing in the blood analyzer 1 is terminated. In the measurement unit 2, after the measurement data is transmitted to the data processing unit 3 at the step S32, whether or not a shutdown instruction from the user has been received is determined at a step S33. When the shutdown instruction has not been received, the control portion 8 moves to the step S21. When the shutdown instruction has been received, an operation of the measurement unit 2 of the sample analysis processing in the blood analyzer 1 is terminated.

According to this embodiment, as hereinabove described, the WBC classification measurement portion 5 generating the side fluorescent light signals, the forward scattered light signals and the side scattered light signals from the measurement sample prepared from the blood sample and the hemolytic agent 100 free from a labeling substance is provided, whereby the side fluorescent light signals, the forward scattered light signals and the side scattered light signals can be obtained by employing intrinsic fluorescence of the eosinophils in the measurement sample without labeling on the measurement sample. The CPU 31 classifying the white blood cells in the measurement sample into four groups of the monocytes, the neutrophils, the eosinophils and the group of the lymphocytes and the basophils on the basis of the side fluorescent light signals, the forward scattered light signals and the side scattered light signals is provided, whereby the white blood cells can be classified into four groups without employing a labeling substance, and hence it is not necessary to include a labeling substance in the hemolytic agent 100. Thus, the white blood cells in the measurement sample can be classified into four groups employing the hemolytic agent 100 having a simple composition free from a labeling substance.

According to this embodiment, the DC measurement portion 6 performing blood cell measurement by the sheath flow DC detection method is provided, and the CPU 31 is configured to classify the white blood cells in the measurement sample into the lymphocytes and the others on the basis of the measurement data by the DC measurement portion 6 and classify the white blood cells into five groups of the lymphocytes, the basophils, the monocytes, the neutrophils and the eosinophils from this classification result and a classification result based on the side fluorescent light signals, the forward scattered light signals and the side scattered light signals, whereby the white blood cells in the measurement sample can be classified into five groups employing the hemolytic agent 100 having a simple composition containing no the side fluorescent light signals, the forward scattered light signals and the side scattered light signals.

In the blood analysis method according to this embodiment, as hereinabove described, the step of generating the side fluorescent light signals, the forward scattered light signals and the side scattered light signals from the measurement sample free from a labeling substance is provided, whereby the side fluorescent light signals, the forward scattered light signals and the side scattered light signals can be obtained by employing intrinsic fluorescence of the eosinophils in the measurement sample without labeling on the measurement sample. The step of classifying the white blood cells in the measurement sample into four groups of the monocytes, the neutrophils, the eosinophils and the group of the lymphocytes and the basophils on the basis of the side fluorescent light signals, the forward scattered light signals and the side scattered light signals is provided, whereby the white blood cells can be classified into four groups without employing a labeling substance, and hence it is not necessary to include a labeling substance in the hemolytic agent 100. Thus, the white blood cells in the measurement sample can be classified into four groups employing the hemolytic agent 100 having a simple composition free from a labeling substance.

The step of generating the side fluorescent light signals, the forward scattered light signals and the side scattered light signals from the measurement sample free from a labeling substance is provided in the blood analysis method employing the hemolytic agent 100 according to this embodiment, whereby the side fluorescent light signals, the forward scattered light signals and the side scattered light signals can be obtained by employing intrinsic fluorescence of the eosinophils in the measurement sample without labeling on the measurement sample. Further, the step of classifying the white blood cells in the measurement sample into four groups of the monocytes, the neutrophils, the eosinophils and the group of the lymphocytes and the basophils on the basis of the side fluorescent light signals, the forward scattered light signals and the side scattered light signals is provided in the blood analysis method employing this hemolytic agent 100, whereby the white blood cells can be classified into four groups without employing a labeling substance, and hence it is not necessary to include a labeling substance in the hemolytic agent 100. In this way, the white blood cells in the measurement sample can be classified into four groups employing the hemolytic agent 100 having a simple composition free from a labeling substance.

The hemolytic agent 100 free from a labeling substance according to this embodiment is employed to classify the white blood cells into four groups of the monocytes, the neutrophils, the eosinophils and the group of the lymphocytes and the basophils employing the side fluorescent light signals, the forward scattered light signals and the side scattered light signals, as hereinabove above, whereby the white blood cells can be classified into four groups without employing a labeling substance, and hence it is not necessary to include a labeling substance in the hemolytic agent 100. In other words, the white blood cells in the measurement sample can be classified into four groups employing the hemolytic agent 100 having a simple composition free from a labeling substance.

According to this embodiment, as hereinabove described, the CPU 31 classifying the white blood cells in the first measurement sample into at least four groups of the monocytes, the neutrophils, the eosinophils and the others on the basis of the side fluorescent light signals, the forward scattered light signals and the side scattered light signals generated from the first measurement sample containing the blood sample and the hemolytic agent 100 by the WBC classification measurement portion 5 and acquiring the hemoglobin concentration in the second measurement sample on the basis of the absorbance measured from the second measurement sample containing the blood sample and the same hemolytic agent 100 as the aforementioned hemolytic agent 100 by the HGB measurement portion 7 is provided, whereby the hemolytic agent for classifying the white blood cells into four groups and the hemolytic agent for acquiring the hemoglobin concentration can be rendered common, and hence it is not necessary to develop more than one type of a hemolytic agent (reagent) having a different composition to classify the white blood cells and acquire the hemoglobin concentration. Thus, the white blood cells in the measurement sample can be classified into four groups and the hemoglobin concentration in the measurement sample can be acquired while reducing a burden on the user due to the development of the reagent.

According to this embodiment, the CPU 31 is configured to classify the white blood cells in the second measurement sample into the lymphocytes and the others on the basis of the measurement data obtained by the DC measurement portion 6 and classify the white blood cells in the measurement sample into at least five groups of the lymphocytes, the basophils, the monocytes, the neutrophils and the eosinophils on the basis of this classification result and the aforementioned classification result of the four groups of the white blood cells, whereby the DC measurement portion 6 can classify the white blood cells into the lymphocytes and the others employing the second measurement sample identical to the measurement sample employed to acquire the hemoglobin concentration, and hence the white blood cells can be classified into five groups without preparing a measurement sample having a different composition separately.

In the blood analysis method according to this embodiment, as hereinabove described, the step of classifying the white blood cells in the first measurement sample into at least four groups of the monocytes, the neutrophils, the eosinophils, the others on the basis of the side fluorescent light signals, the forward scattered light signals and the side scattered light signals generated from the first measurement sample containing the blood sample and the hemolytic agent 100 by the WBC classification measurement portion 5 and the step of acquiring the hemoglobin concentration in the second measurement sample on the basis of the absorbance measured from the second measurement sample containing the blood sample and the same hemolytic agent 100 as the aforementioned hemolytic agent 100 by the HGB measurement portion 7 are provided, whereby the hemolytic agent for classifying the white blood cells into four groups and the hemolytic agent for acquiring the hemoglobin concentration can be rendered common, and hence it is not necessary to develop more than one type of a hemolytic agent (reagent) having a different composition to classify the white blood cells and acquire the hemoglobin concentration. Thus, the white blood cells in the measurement sample can be classified into four groups and the hemoglobin concentration in the measurement sample can be acquired while reducing a burden on the user due to the development of the reagent.

The hemolytic agent according to this embodiment is employed in the blood analysis method comprising the step of classifying the white blood cells in the first measurement sample into at least four groups of the monocytes, the neutrophils, the eosinophils, the others on the basis of the side fluorescent light signals, the forward scattered light signals and the side scattered light signals generated from the first measurement sample containing the blood sample and the hemolytic agent 100 by the WBC classification measurement portion 5 and the step of acquiring the hemoglobin concentration in the second measurement sample on the basis of the absorbance measured from the second measurement sample containing the blood sample and the same hemolytic agent 100 as the aforementioned hemolytic agent 100 by the HGB measurement portion 7, as hereinabove described, whereby the hemolytic agent for classifying the white blood cells into four groups and the hemolytic agent for acquiring the hemoglobin concentration can be rendered common, and hence it is not necessary to develop more than one type of a hemolytic agent (reagent) having a different composition to classify the white blood cells and acquire the hemoglobin concentration. Thus, the white blood cells in the measurement sample can be classified into four groups and the hemoglobin concentration in the measurement sample can be acquired while reducing a burden on the user due to the development of the reagent.

The hemolytic agent according to this embodiment includes the cationic surfactant, and is employed to measure the hemoglobin concentration and classify the white blood cells into at least the lymphocytes, the basophils, the monocytes, the neutrophils and the eosinophils, as hereinabove described, whereby the hemolytic agent for classifying the white blood cells into four groups and the hemolytic agent for acquiring the hemoglobin concentration can be rendered common, and hence it is not necessary to develop more than one type of a hemolytic agent (reagent) having a different composition to classify the white blood cells and acquire the hemoglobin concentration. Thus, the white blood cells in the measurement sample can be classified into four groups and the hemoglobin concentration in the measurement sample can be acquired while reducing a burden on the user due to the development of the reagent.

EXAMPLE

Next, results of verification of the correlations between measurement results obtained by a method described in the aforementioned embodiment and measurement results obtained by a multiparameter automated hematology analyzer Model XE-2100 (SYSMEX CORPORATION) are described with reference to FIGS. 24 to 28. Measurement by the method described in the aforementioned embodiment and measurement by the multiparameter automated hematology analyzer Model XE-2100 are performed with respect to the same specimen in a plurality of blood samples. FIGS. 24 to 28 show correlation diagrams between the measurement results of hemoglobin, a group of lymphocytes and basophils, monocytes, neutrophils and eosinophils, respectively. Referring to each of FIGS. 24 to 28, the axis of ordinate shows the measurement result obtained by the method described in the aforementioned embodiment and the axis of abscissa shows the measurement result obtained by the multiparameter automated hematology analyzer Model XE-2100. As shown in these figures, referring to hemoglobin, the correlation coefficient r is 0.992, referring to the group of lymphocytes and basophils, the correlation coefficient r is 0.968, referring to monocytes, the correlation coefficient r is 0.796, referring to neutrophils, the correlation coefficient r is 0.946 and referring to eosinophils, the correlation coefficient r is 0.892, and all of these resulted in high correlation.

The embodiment disclosed this time must be considered as illustrative in all points and not restrictive. The range of the present invention is shown not by the above description of the embodiment but by the scope of claims for patent, and all modifications within the meaning and range equivalent to the scope of claims for patent are further included.

For example, while the example of storing the hemolytic agent employed for the WBC detection, the HGB detection, the WBC classification detection and the malaria detection in the single hemolytic agent container has been shown in the aforementioned embodiment, the inventions according to the first to fourth aspects are not restricted to this, but separate hemolytic agents may be prepared for the respective detections and stored in separate hemolytic agent containers. At this time, the hemolytic agents employed for the respective detections may be different types of hemolytic agents. Further, the hemolytic agents stored in the respective hemolytic agent containers may be diluted by respective predetermined dilution magnifications.

While the semiconductor laser light source having the blue-violet semiconductor laser element has been shown as an example of a light source in the aforementioned embodiment, the present invention is not restricted to this, but a light source having another laser element other than the blue-violet semiconductor laser element, such as a blue semiconductor laser element or an argon laser element may be employed.

While the semiconductor laser light source emitting the blue-violet laser beam having a wavelength of about 405 nm has been shown as an example of a light source in the aforementioned embodiment, the inventions according to the first to fourth aspects are not restricted to this, but another light source other than the semiconductor laser light source may be employed so far as the light source emits light having a wavelength of at least 350 nm and not more than 500 nm. According to this structure, light in a short-wavelength range capable of acquiring fluorescent information based on intrinsic fluorescence of the eosinophils can be emitted to the measurement sample.

While the example of performing each detection processing in the order of the RBC/PLT detection, the WBC detection, the HGB detection, the WBC classification detection and the malaria detection from the earliest in the sample analysis processing has been shown in the aforementioned embodiment, the present invention is not restricted to this, but each detection processing may be performed in another order other than the aforementioned order in the sample analysis processing. Also, the order of white blood cell classification processing, malaria classification processing, red blood cell count/platelet count calculation processing and hemoglobin amount calculation processing in the sample analysis processing can be properly varied.

While the example of connecting the single hemolytic agent container serving as a reagent container, storing the hemolytic agent commonly employed for the WBC detection, the HGB detection, the WBC classification detection and the malaria detection to the sample supply portion has been shown in the aforementioned embodiment, the inventions according to the fifth to eighth aspects are not restricted to this, but four hemolytic agent containers may be connected to the sample supply portion so as to store the hemolytic agents employed for the respective detections separately, or a hemolytic agent employed for any of the aforementioned four detections may be stored in a common hemolytic agent container and two or three hemolytic agent containers may be connected to the sample supply portion. Alternatively, more than four hemolytic agent containers may be connected to the sample supply portion. At this time, if the hemolytic agents stored in the respective hemolytic agent containers are diluted by respective predetermined dilution magnifications, no steps to dilute the hemolytic agents by desired dilution magnifications may be provided separately when preparing the measurement samples employed for the respective detections.

While the hemolytic agent free from a labeling substance has been shown as an example of a hemolytic agent in the aforementioned embodiment, the inventions according to the fifth to eighth aspects are not restricted to this, but the hemolytic agent may contain a labeling substance.

While the HGB measurement portion measuring an absorbance serving as transmitted light information has been shown as an example of a second light information generation portion in the aforementioned embodiment, the present invention is not restricted to this, but the HGB measurement portion may generate scattered light information. In this case, the CPU in the data processing unit acquires a hemoglobin concentration on the basis of the scattered light information generated by the HGB measurement portion.

While the hemolytic agent including the cationic surfactant (lauryl trimethyl ammonium chloride; 34.1 mM, stearyl trimethyl ammonium chloride; 1.7 mM), which is an alkyl trimethyl ammonium salt and the number of carbons of the alkyl group of which is at least twelve and not more than eighteen, has been shown as an example of a hemolytic agent in the aforementioned embodiment, the present invention is not restricted to this, but a hemolytic agent including a cationic surfactant having a concentration other than the aforementioned concentration may be employed so far as a concentration of the cationic surfactant (the total of lauryl trimethyl ammonium chloride and stearyl trimethyl ammonium chloride in the aforementioned embodiment) in the WBC measurement sample (for classification) is at least 0.62 mM and not more than 2.15 mM. According to the aforementioned embodiment, the measurement sample is prepared by diluting the hemolytic agent by 25 times, and hence a concentration of the cationic surfactant in the hemolytic agent is 15.5 nM when the concentration of the cationic surfactant in the WBC measurement sample (for classification) is 0.62 mM, and the concentration of the cationic surfactant in the hemolytic agent is 53.75 nM when the concentration of the cationic surfactant in the WBC measurement sample (for classification) is 2.15 mM. If a cationic surfactant, the number of carbons of the alkyl group of which is at least eight and not more than ten is employed instead of the aforementioned hemolytic agent, the measurement sample can be measured even when a concentration of the cationic surfactant in the WBC measurement sample (for classification) is 2.15 mM or more.

Experimental results when fluctuating the concentration of the cationic surfactant in the hemolytic agent in the blood analyzer according to the embodiment of the present invention are described. In the experiment, a plurality of experimental results in which the concentrations of the cationic surfactants in the hemolytic agents are slightly different from each other have been obtained, but here two experimental results when the hemolytic agent in which the concentration of the cationic surfactant in the WBC measurement sample (for classification) is 2.15 mM is employed and when the hemolytic agent in which the concentration of the cationic surfactant in the WBC measurement sample (for classification) is 0.62 mM is employed are described on behalf of the plurality of experimental results.

Figure 18:
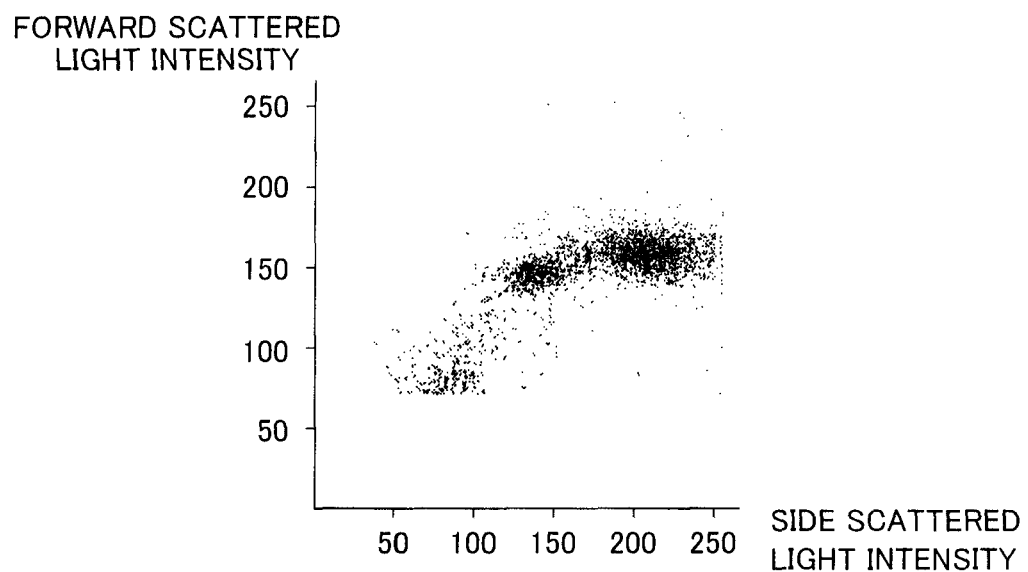
FIG. 18 is a diagram showing an experimental result when employing a hemolytic agent in which a concentration of a cationic surfactant in a WBC measurement sample (for classification) is 2.15 mM in the blood analyzer according to the embodiment shown in FIG. 1.
Figure 19:
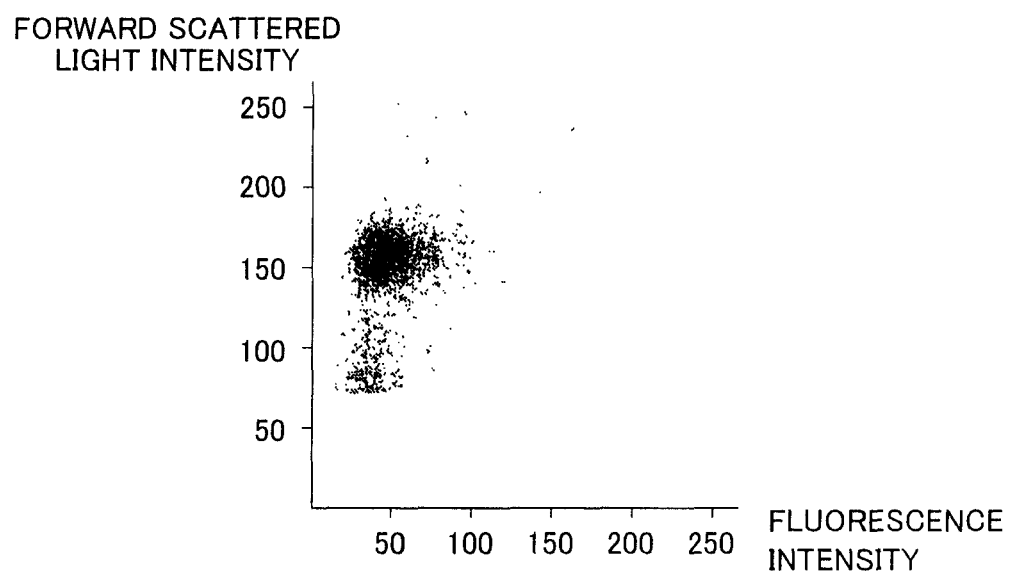
FIG. 19 is a diagram showing an experimental result when employing a hemolytic agent in which a concentration of a cationic surfactant in the WBC measurement sample (for classification) is 2.15 mM in the blood analyzer according to the embodiment shown in FIG. 1.
Figure 20:
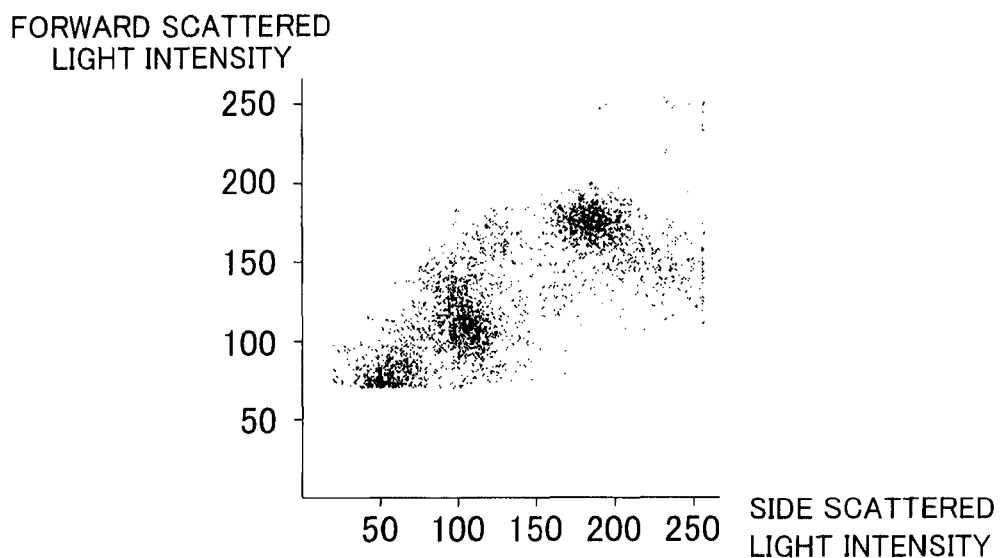
FIG. 20 is a diagram showing an experimental result when employing a hemolytic agent in which a concentration of a cationic surfactant in the WBC measurement sample (for classification) is 0.62 mM in the blood analyzer according to the embodiment shown in FIG. 1.
Figure 21:
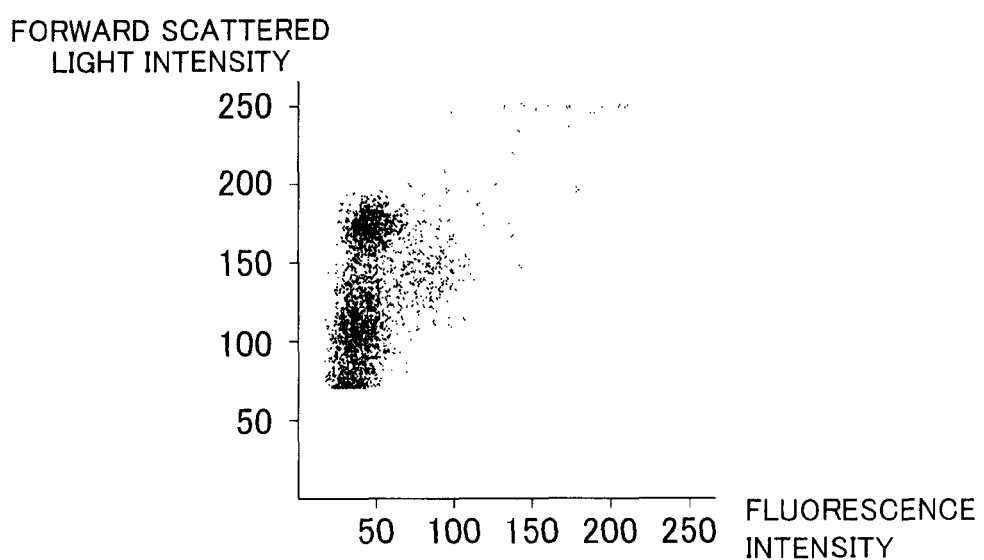
FIG. 21 is a diagram showing an experimental result when employing a hemolytic agent in which a concentration of a cationic surfactant in the WBC measurement sample (for classification) is 0.62 mM in the blood analyzer according to the embodiment shown in FIG. 1.

As shown in FIGS. 18 and 20, the white blood cells can be classified into three groups of the group of lymphocytes and basophils, the monocytes and the granulocytes (the group of neutrophils and eosinophils) on the scattergram. As shown in FIGS. 19 and 21, the white blood cells can be classified into the eosinophils and the others on the scattergram. Further, the white blood cells can be classified into four groups of the group of lymphocytes and basophils, the monocytes, the neutrophils and the eosinophils from these classification results. Therefore, the white blood cells can be conceivably classified into four groups in a case where the concentration of the cationic surfactant in the WBC measurement sample (for classification) is in the range of at least 0.62 mM and not more than 2.15 mM.

What is claimed is:

1. A blood analyzer comprising: a sample preparation portion configured to prepare a first measurement sample containing a blood sample and a hemolytic agent and a second measurement sample containing said blood sample and the same hemolytic agent as said hemolytic agent, wherein a dilution magnification of said hemolytic agent in said second measurement sample is different from a dilution magnification of said hemolytic agent in said first measurement sample;
   a first measurement portion including a flow cell configured to connect with the sample preparation portion, a light source that irradiates light to the flow cell, and first, second and third light detectors, wherein the first, second and third light detectors respectively receive a first type of scattered light, a second type of scattered light, and fluorescence emitted from the flow cell and the light detectors output signals according to intensities of the received light;
   a second measurement portion including a cell configured to connect with the sample preparation portion and a light source that irradiates light to the cell and generating either transmitted light information or scattered light information according to transmitted light or scattered light from the cell; and
   a data processing unit is connected to the first and second measurement portions via a communication interface and comprises a memory storing a computer program, wherein the data processing unit is configured to execute the computer program from the memory, wherein the computer program is programmed to perform a first analysis operation and a second analysis operation steps, wherein;
   (A) the data processing unit is configured to perform the first analysis operation, the first analysis operation includes steps of:
   receiving signals from the first measurement portion via the communication interface;
   determining a proportion of monocyte, granulocyte and a group of lymphocyte and basophil contained in the first measurement sample based on the signals output from the first and second light detectors;
   determining a proportion of eosinophil in the first measurement sample based on the signals output from the first and third light detectors; and
   calculating a proportion of monocyte, neutrophil, and eosinophil in the first measurement sample based on the determination results, and
   (B) the data processing unit is configured to perform the second analysis operation, the second analysis operation includes steps of:
   receiving transmitted light information or scattered light information generated by the second measurement portion via the communication interface; and
   acquiring a hemoglobin concentration of the second measurement sample on the basis of the received information from the second measurement portion.

2. The blood analyzer according to claim 1, further comprising an electrical information generation portion including a second flow cell configured to connect with the sample preparation portion and to generate electrical information of a part of the second measurement sample, wherein
   the data processing unit is connected to the electrical information generation portion via the communication interface, and
   the data processing unit is further configured to perform further first analysis operation steps of:
   receiving electrical information from the electrical information generation portion via the communication interface, and
   determining a proportion of lymphocyte in the blood sample based on the electrical information; and determining a proportion of lymphocyte, basophil, monocyte, neutrophil and eosinophil in the blood sample on the basis of the determination results.

3. The blood analyzer according to claim 2, wherein said sample preparation portion is further configured to prepare a third measurement sample from said blood sample,
   said electrical information generation portion is configured to generate electrical information of said third measurement sample, and
   the data processing unit is configured to execute the computer program to further perform a third analysis operation, wherein the third analysis operation includes steps of:
   receiving electrical information of said third measurement sample via the communication interface; and
   counting a number of red blood cells and a number of platelets in said third measurement sample on the basis of said electrical information generated from said third measurement sample by said electrical information generation portion.

4. The blood analyzer according to claim 1, wherein said dilution magnification of said hemolytic agent in said second measurement sample is smaller than said dilution magnification of said hemolytic agent in said first measurement sample.

5. The blood analyzer according to claim 1, wherein said sample preparation portion is configured to prepare said first measurement sample by mixing said blood sample, said hemolytic agent stored in a predetermined reagent container and a predetermined quantity of diluted solution and to prepare said second measurement sample by mixing said blood sample, said hemolytic agent stored in said predetermined reagent container and a quantity of said diluted solution smaller than said predetermined quantity.

6. The blood analyzer according to claim 5, wherein said sample preparation portion is configured to prepare said second measurement sample by adding said hemolytic agent to a mixture of said diluted solution and said blood sample.

7. The blood analyzer according to claim 1, wherein said sample preparation portion includes a first chamber employed for diluting said hemolytic agent to be used in preparation of the first measurement sample and a second chamber employed for diluting said hemolytic agent to be used in preparation of the second measurement sample, and is configured to prepare said second measurement sample by mixing at least said blood sample and said hemolytic agent in the second chamber.

8. The blood analyzer according to claim 7, wherein said hemolytic agent stored in said second chamber is diluted by substantially 3 times.

9. The blood analyzer according to claim 1, wherein said hemolytic agent includes a cationic surfactant.

10. The blood analyzer according to claim 1, wherein said hemolytic agent is free from a labeling substance.

11. The blood analyzer according to claim 1, wherein said third light detector is configured to output a signal according to an intensity of intrinsic fluorescence of eosinophils in said first measurement sample.

12. The blood analyzer according to claim 1, wherein the first light detector is arranged to receive forward scattered light emitted along a traveling direction of a beam of light emitted from said light source; and
   the second light detector is arranged to receive side scattered light emitted along a direction substantially perpendicular to the traveling direction of the beam of light emitted from said light source.

13. The blood analyzer according to claim 1, wherein the beam of light which is emitted from said light source has a wavelength of at least 350 nm and not more than 500 nm.

14. The blood analyzer according to claim 13, wherein said light source has a blue-violet semiconductor laser element.

* * * * *